United States Patent
Bindschaedler et al.

(10) Patent No.: US 9,936,702 B2
(45) Date of Patent: Apr. 10, 2018

(54) SUSPENSION CONCENTRATE COMPOSITION COMPRISING ISOTHIAZOLINE INSECTICIDE AND ACTIVATED CHARCOAL

(71) Applicant: BASF SE, Ludwigshafen (DE)

(72) Inventors: Pascal Bindschaedler, Roemerberg (DE); Anna Cristadoro, Waldems (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/899,859

(22) PCT Filed: Jun. 11, 2014

(86) PCT No.: PCT/EP2014/062071
§ 371 (c)(1),
(2) Date: Dec. 18, 2015

(87) PCT Pub. No.: WO2014/202437
PCT Pub. Date: Dec. 24, 2014

(65) Prior Publication Data
US 2016/0143283 A1 May 26, 2016

Related U.S. Application Data

(60) Provisional application No. 61/837,667, filed on Jun. 21, 2013.

(30) Foreign Application Priority Data

Jul. 4, 2013 (EP) .................................... 13175019

(51) Int. Cl.
*A01N 43/80* (2006.01)
(52) U.S. Cl.
CPC .................................... *A01N 43/80* (2013.01)
(58) Field of Classification Search
USPC ....................................................... 514/342
See application file for complete search history.

(56) References Cited

U.S. PATENT DOCUMENTS 4,971,796 A * 11/1990 Sjogren .................. A01N 25/26
424/408

FOREIGN PATENT DOCUMENTS

| GB | 2 172 804 A | | 10/1986 |
|---|---|---|---|
| GB | 2172804 | * | 10/1986 |
| WO | WO2013/037626 | * | 3/2013 |
| WO | WO 2013/037626 A1 | | 3/2013 |
| WO | WO2013/092943 | * | 6/2013 |
| WO | WO 2013/092943 A1 | | 6/2013 |

OTHER PUBLICATIONS

Patani et. al. (Chem. Rev. (1996) 96:3147-3176).*
J. G. Cannon, Chapter Nineteen in Burger's Medicinal Chemistry and Drug Discovery, Fifth Edition, vol. I: Principles and Practice, Wiley-Interscience 1995, pp. 783-802.*
European Search Report dated Sep. 5, 2013 for EP Application No. 13 17 5019.
International Search Report dated Jul. 16, 2014 for PCT Application No. PCT/EP2014/062071.
Silverman, The Organic Chemistry of Drug Design and Drug Action, II. Drug Development: Lead Modification, $2^{nd}$ Edition, 2004, Elsevier Academic Press, pp. 29-34.

* cited by examiner

Primary Examiner — Marcos L Sznaidman
(74) Attorney, Agent, or Firm — Brinks Gilson & Lione

(57) ABSTRACT

Subject matter of the present invention is a suspension concentrate composition comprising an a) isothiazoline insecticide and b) activated charcoal, wherein the composition is substantially free of a non-polar solvent. The invention further relates to a process for the preparation of said composition; a suspension obtainable by mixing water, an isothiazoline insecticide and activated charcoal; and to a method for controlling undesired attack by insects or mites, where the suspension concentrate composition or the suspension is allowed to act on the respective pests, their environment or on the crop plants to be protected from the respective pests.

10 Claims, No Drawings

SUSPENSION CONCENTRATE COMPOSITION COMPRISING ISOTHIAZOLINE INSECTICIDE AND ACTIVATED CHARCOAL

This application is a National Stage application of International Application No. PCT/EP2014/062071, filed Jun. 11, 2014, which claims the benefit of U.S. Provisional Application No. 61/837,667, filed Jun. 21, 2013. This application also claims priority under 35 U.S.C. § 119 to European Patent Application No. 13175019.2, filed Jul. 4, 2013.

Subject matter of the present invention is a suspension concentrate composition comprising a) an isothiazoline insecticide, and b) activated charcoal as defined herein, wherein the composition is substantially free of a non-polar solvent. The invention further relates to a process for the preparation of said composition; a suspension obtainable by mixing water, and the components a) and b); and to a method for controlling undesired attack by insects or mites, where the solution is allowed to act on the respective pests, their environment or on the crop plants to be protected from the respective pests. The present invention comprises combinations of preferred features with other preferred features.

It was an object of the present invention to provide a suspension concentrate composition comprising an isothiazoline insecticide, which is poorly water soluble (less than 50 ppm solubility in water) and susceptible to ultraviolet degradation, which overcomes these disadvantages.

The object was achieved by a suspension concentrate composition comprising,
a) an isothiazoline insecticide, and
b) activated charcoal, wherein the composition is substantially free of a non-polar solvent.

In one form, the isothiazoline insecticide and activated charcoal may form a complex, wherein the complex is substantially free of a non-polar solvent. The complex may form with adsorption of crystalline isothiazoline insecticide into pores of the activated charcoal and may involve non-covalent interactions, including electrostatic interactions between the inner walls of the activated charcoal pore and the isothiazoline insecticide. The weight percent ratio of insecticide:charcoal can range anywhere from 1-10 wt % insecticide:10-1 wt % charcoal. For example, the ratio can be 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, or 10:1.

The suspension concentrate composition can comprise 1% to 50% by weight of the isothiazoline insecticide, preferably 2% to 30% and most preferably 3 to 20%.

The suspension concentrate composition is substantially free of a non-polar solvent. Non-polar solvents may have a solubility in water of up to 10 g/l at 20° C., preferably up to 2 g/l, and in particular up to 0.5 g/l. Examples of non-polar solvents are paraffinic and aromatic solvents, petroleum oils, and/or mixtures thereof. The suspension concentrate composition comprises not more than 1% by weight, preferably not more than 0.5% by weight and in particular not more than 0.1% by weight of a non-polar solvent. In special form, the concentrate comprises not more than 0.05% by weight and in particular not more than 0.01% by weight of a non-polar solvent.

Typically, the isothiazoline insecticide is poorly water soluble, yet in the present invention it is not dissolved in a non-polar solvent prior to mixing with activated charcoal; unlike typical approaches to solubilize poorly water soluble compounds in a non-polar solvent prior to mixing with activated charcoal. The water solubility of the isothiazoline insecticide may be up to 50 ppm, preferably up to 20 ppm, and in particular up to 5 ppm at 20° C. The isothiazoline insecticide is thus used in crystalline form in the preparation of the suspension concentrate composition of the present invention. The efficacy of the insecticide is maintained in the composition comprising the isothiazoline insecticide and activated charcoal.

The isothiazoline insecticide is a compound of the formula I:

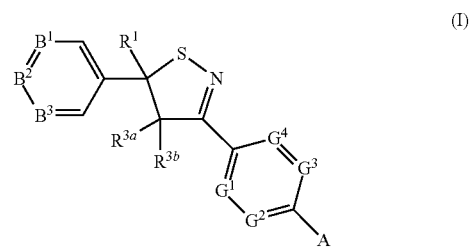

wherein
A is a group $A^1$, $A^2$, $A^3$ or $A^4$;
  wherein
  $A^1$ is selected from the group consisting of —C(=NR$^6$)R$^8$, —S(O)$_n$R$^9$ and —N(R$^5$)R$^6$;
  $A^2$ is a group of following formula:

wherein
  # denotes the bond to the aromatic ring of formula (I);
  W is selected from O and S;
  Y is selected from hydrogen, —N(R$^5$)R$^6$ and —OR$^9$;
  $A^3$ is a group of following formula:

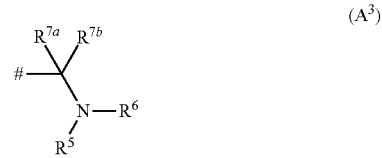

wherein
  # denotes the bond to the aromatic ring of formula (I);
  $A^4$ is a 3-, 4-, 5-, 6- or 7-membered saturated, partially unsaturated or maximally unsaturated heteromonocyclic ring containing 1, 2, 3 or 4 heteroatoms or heteroatom groups selected from N, O, S, NO, SO and SO$_2$, as ring members, or is a 8-, 9- or 10-membered saturated, partially unsaturated or maximally unsaturated heterobicyclic ring containing 1, 2, 3 or 4 heteroatoms or heteroatom groups selected from N, O, S, NO, SO and SO$_2$, as ring members, where the heteromonocyclic or heterobicyclic ring is optionally substituted with one or more substituents $R^{11}$;
$B^1$, $B^2$ and $B^3$ are each independently selected from the group consisting of N and CR$^2$, with the proviso that at most two of $B^1$, $B^2$ and $B^3$ are N;

$G^1$, $G^2$, $G^3$ and $G^4$ are each independently selected from the group consisting of N and $CR^4$, with the proviso that at most two of $G^1$, $G^2$, $G^3$ and $G^4$ are N;

$R^1$ is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl-, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl and —C(=O)$OR^{15}$;

each $R^2$ is independently selected from the group consisting of hydrogen, halogen, cyano, azido, nitro, —SCN, —SF$_5$, $C_1$-$C_6$-alkyl, $C_3$-$C_8$-cycloalkyl, $C_2$-$C_6$-alkenyl, $C_2$-$C_6$-alkynyl, wherein the four last mentioned aliphatic and cycloaliphatic radicals may be partially or fully halogenated and/or may be substituted by one or more radicals $R^8$, —Si($R^{12}$)$_3$, —$OR^9$, —S(O)$_n R^9$, —$NR^{10a}R^{10b}$, phenyl which may be substituted by 1, 2, 3, 4 or 5 radicals $R^{11}$, and a 3-, 4-, 5-, 6- 7-, 8-, 9- or 10-membered saturated, partially unsaturated or maximally unsaturated heteromonocyclic or heterobicyclic ring containing 1, 2, 3 or 4 heteroatoms or heteroatom groups selected from N, O, S, NO, SO and SO$_2$, as ring members, where the heteromono- or heterobicyclic ring may be substituted by one or more radicals $R^{11}$;

$R^{3a}$, $R^{3b}$ are each independently selected from the group consisting of hydrogen, halogen, hydroxyl, —CO$_2 R^{3d}$, $C_1$-$C_3$-alkyl, $C_1$-$C_3$-haloalkyl, $C_2$-$C_3$-alkenyl, $C_2$-$C_3$-alkynyl, $C_1$-$C_3$-alkoxy, $C_1$-$C_3$-haloalkoxy, $C_1$-$C_3$-alkylthio, $C_1$-$C_3$-haloalkylthio, $C_1$-$C_3$-alkylsulfonyl and $C_1$-$C_3$-haloalkylsulfonyl; or $R^{3a}$ and $R^{3b}$ together form a group =O, =C($R^{3c}$)$_2$, =NOH or =NOCH$_3$;

each $R^{3c}$ is independently selected from the group consisting of hydrogen, halogen, CH$_3$ and CF$_3$;

$R^{3d}$ is selected from the group consisting of hydrogen, $C_1$-$C_6$-alkyl and $C_1$-$C_3$-alkyloxy-$C_1$-$C_3$-alkyl-;

each $R^4$ is independently selected from the group consisting of hydrogen, halogen, cyano, azido, nitro, —SCN, —SF$_5$, $C_1$-$C_6$-alkyl which may be partially or fully halogenated and/or may be substituted by one or more radicals $R^8$, $C_3$-$C_8$-cycloalkyl which may be partially or fully halogenated and/or may be substituted by one or more radicals $R^8$, $C_2$-$C_6$-alkenyl which may be partially or fully halogenated and/or may be substituted by one or more radicals $R^8$, $C_2$-$C_6$-alkynyl which may be partially or fully halogenated and/or may be substituted by one or more radicals $R^8$, —Si($R^{12}$)$_3$, —$OR^9$, —S(O)$_n R^9$, —$NR^{10a}R^{10b}$, phenyl which may be substituted by 1, 2, 3, 4 or 5 radicals $R^{11}$, and a 3-, 4-, 5-, 6- 7-, 8-, 9- or 10-membered saturated, partially unsaturated or maximally unsaturated heteromonocyclic or heterobicyclic ring containing 1, 2, 3 or 4 heteroatoms or heteroatom groups selected from N, O, S, NO, SO and SO$_2$, as ring members, where the heteromonocyclic or heterobicyclic ring may be substituted by one or more radicals $R^{11}$;

each $R^5$ is independently selected from the group consisting of hydrogen, $C_1$-$C_{10}$-alkyl, $C_3$-$C_5$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more substituents $R^8$, and —S(O)$_n R^9$, each $R^6$ is independently selected from the group consisting of hydrogen, cyano, $C_1$-$C_{10}$-alkyl, $C_3$-$C_8$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted by one or more substituents $R^8$, —$OR^9$, —$NR^{10a}R^{10b}$, —S(O)$_n R^9$, —C(=O)$NR^{10a}$N($R^{10a}$)$R^{10b}$, —Si($R^{12}$)$_3$, —C(=O)$R^8$, phenyl which may be substituted with 1, 2, 3, 4, or 5 substituents $R^{11}$, and a 3-, 4-, 5-, 6-, 7-, 8-, 9- or 10-membered saturated, partially unsaturated or maximally unsaturated heteromonocyclic or heterobicyclic ring containing 1, 2, 3 or 4 heteroatoms or heteroatom groups independently selected from N, O, S, NO, SO and SO$_2$, as ring members, where the heteromonocyclic or heterobicyclic ring may be substituted with one or more substituents $R^{11}$;

or $R^5$ and $R^6$, together with the nitrogen atom to which they are bound, form a 3-, 4-, 5-, 6-, 7- or 8-membered saturated, partially unsaturated or maximally unsaturated heterocyclic ring, where the ring may further contain 1, 2, 3 or 4 heteroatoms or heteroatom-containing groups selected from O, S, N, SO, SO$_2$, C=O and C=S as ring members, wherein the heterocyclic ring may be substituted with 1, 2, 3, 4 or 5 substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the aliphatic or cycloaliphatic moieties in the twelve last-mentioned radicals may be substituted by one or more radicals $R^8$, and phenyl which may be substituted with 1, 2, 3, 4 or 5 substituents $R^{11}$;

or $R^5$ and $R^6$ together form a group =C($R^8$)$_2$, =S(O)$_m$($R^9$)$_2$, =$NR^{10a}$ or =$NOR^9$;

$R^{7a}$, $R^{7b}$ are each independently selected from the group consisting of hydrogen, halogen, cyano, $C_1$-$C_6$-alkyl, $C_3$-$C_8$-cycloalkyl, $C_2$-$C_6$-alkenyl and $C_2$-$C_6$-alkynyl, wherein the four last-mentioned aliphatic and cycloaliphatic radicals may be partially or fully halogenated and/or may be substituted by one or more radicals $R^8$;

each $R^8$ is independently selected from the group consisting of cyano, azido, nitro, —SCN, —SF$_5$, $C_3$-$C_8$-cycloalkyl, $C_3$-$C_8$-halocycloalkyl, where the cycloaliphatic moieties in the two last-mentioned radicals may be substituted by one or more radicals $R^{13}$;

—Si($R^{12}$)$_3$, —$OR^9$, —OSO$_2 R^9$, —S(O)$_n R^9$, —N($R^{10a}$)$R^{10b}$, —C(=O)N($R^{10a}$)$R^{10b}$,

—C(=S)N($R^{10a}$)$R^{10b}$, —C(=O)$OR^9$, phenyl, optionally substituted with 1, 2, 3, 4 or 5 substituents $R^{16}$, and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and SO$_2$, as ring members, where the heterocyclic ring is optionally substituted with one or more substituents $R^{16}$, or two $R^8$ present on the same carbon atom of an alkyl, alkenyl, alkynyl or cycloalkyl group together form a group =O, =C($R^{13}$)$_2$; =S; =S(O)$_m$($R^{15}$)$_2$, =S(O)$_m R^{15}$N($R^{14a}$)$R^{14b}$, =$NR^{10a}$, =$NOR^9$; or =NN($R^{10a}$)$R^{10b}$;

or two radicals $R^8$, together with the carbon atoms of an alkyl, alkenyl, alkynyl or cycloalkyl group which they are bonded to, form a 3-, 4-, 5-, 6-, 7- or 8-membered saturated or partially unsaturated carbocyclic or heterocyclic ring, where the heterocyclic ring comprises 1, 2, 3 or 4 heteroatoms or heteroatom groups independently selected from N, O, S, NO, SO and $SO_2$, as ring members, and where the carbocyclic or heterocyclic ring is optionally substituted with one or more substituents $R^{16}$; and $R^8$ as a substituent on a cycloalkyl ring is additionally selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $0_2$-$C_6$-haloalkynyl, where the aliphatic moieties in these six radicals may be substituted by one or more radicals $R^{13}$; and $R^8$ in the groups —C(=$NR^6$)$R^8$, —C(=O)$R^8$ and =O($R^8$)$_2$ is additionally selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl and $C_2$-$C_6$-haloalkynyl, where the aliphatic moieties in the six last-mentioned radicals may be substituted by one or more radicals $R^{13}$;

each $R^9$ is independently selected from the group consisting of hydrogen, cyano, $C_1$-$C_6$-alkyl, $C_1$-$C_6$-haloalkyl, $C_3$-$C_8$-cycloalkyl, $C_3$-$C_8$-cycloalkyl-$C_1$-$C_4$-alkyl-, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the nine last-mentioned radicals may be substituted by one or more radicals $R^{13}$,
—$C_1$-$C_6$-alkyl-C(=O)$OR^{15}$, —$C_1$-$C_6$-alkyl-C(=O)N($R^{14a}$)$R^{14b}$,
—$C_1$-$C_6$-alkyl-C(=S)N($R^{14a}$)$R^{14b}$, —$C_1$-$C_6$-alkyl-C(=$NR^{14}$)N($R^{14a}$)$R^{14b}$,
—Si($R^{12}$)$_3$, —S(O)$_n$$R^{15}$, —S(O)$_n$N($R^{14a}$)$R^{14b}$,
—N($R^{10a}$)$R^{10b}$, —N=C($R^{13}$)$_2$, —C(=O)$R^{13}$,
—C(=O)N($R^{14a}$)$R^{14b}$, —C(=S)N($R^{14a}$)$R^{14b}$,
—C(=O)$OR^{15}$, phenyl, optionally substituted with one or more substituents $R^{16}$; and a 3-, 4-, 5-, 6- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring is optionally substituted with one or more substituents $R^{16}$; and $R^9$ in the groups —S(O)$_n$$R^9$ and —$OSO_2$$R^9$ is additionally selected from the group consisting of $C_1$-$C_6$-alkoxy and $C_1$-$C_6$-haloalkoxy;

$R^{10a}$, $R^{10b}$ are selected independently from one another from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, where the aliphatic and cycloaliphatic moieties in the eight last-mentioned radicals may be substituted by one or more radicals $R^{13}$;
—$C_1$-$C_6$-alkyl-C(=O)$OR^{15}$, —$C_1$-$C_6$-alkyl-C(=O)N($R^{14a}$)$R^{14b}$, —$C_1$-$C_6$-alkyl-C(=S)N($R^{14a}$)$R^{14b}$,
—$C_1$-$C_6$-alkyl-C(=$NR^{14}$)N($R^{14a}$)$R^{14b}$, $C_1$-$C_6$-alkoxy, $C_1$-$C_6$-haloalkoxy, $C_1$-$C_6$-alkylthio, $C_1$-$C_6$-haloalkylthio,
—S(O)$_n$$R^{15}$, —S(O)$_n$N($R^{14a}$)$R^{14b}$, —C(=O)$R^{13}$,
—C(=O)$OR^{15}$, —C(=O)N($R^{14a}$)$R^{14b}$,
—C(=S)$R^{13}$, —C(=S)$SR^{15}$, —C(=S)N($R^{14a}$)$R^{14b}$,
—C(=$NR^{14}$)$R^{13}$;

phenyl, optionally substituted with 1, 2, 3 or 4, substituents $R^{16}$; and a 3-, 4-, 5-, 6- or 7-membered saturated, partially unsaturated or maximally unsaturated heterocyclic ring comprising 1, 2, 3 or 4 heteroatoms or heteroatom groups selected from N, O, S, NO, SO and $SO_2$, as ring members, where the heterocyclic ring is optionally substituted with one or more substituents $R^{16}$;

or $R^{10a}$ and $R^{10b}$ form together with the nitrogen atom they are bonded to a 3-, 4-, 5-, 6-, 7- or 8-membered saturated, partially unsaturated or maximally unsaturated heterocyclic ring, wherein the heterocyclic ring may additionally contain one or two heteroatoms or heteroatom groups selected from N, O, S, NO, SO and $SO_2$, as ring members, where the heterocyclic ring optionally carries one or more substituents selected from halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_5$-cycloalkyl, $C_3$-$C_5$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl, optionally substituted with 1, 2, 3, 4 or 5 substituents $R^{16}$, and a 3-, 4-, 5-, 6,- or 7-membered saturated, partially unsaturated or maximally unsaturated heterocyclic ring comprising 1, 2 or 3 heteroatoms or heteroatom groups selected from N, O, S, NO, SO and $SO_2$, as ring members, where the heterocyclic ring optionally carries one or more substituents $R^{16}$;

or $R^{10a}$ and $R^{10b}$ together form a group =C($R^{13}$)$_2$, =S(O)$_m$($R^{15}$)$_2$, =S(O)$_m$$R^{15}$N($R^{14a}$)$R^{14b}$, =$NR^{14}$ or =$NOR^{15}$;

$R^{11}$ is independently selected from the group consisting of halogen, cyano, azido, nitro, —SCN, —$SF_5$, $C_1$-$C_{10}$-alkyl, $C_3$-$C_5$-cycloalkyl, $C_2$-$C_{10}$-alkenyl, $C_2$-$C_{10}$-alkynyl, wherein the four last-mentioned aliphatic and cycloaliphatic radicals may be partially or fully halogenated and/or may be substituted with one or more radicals $R^8$,
—$OR^9$, —$NR^{10a}R^{10b}$, —S(O)$_n$$R^9$, —Si($R^{12}$)$_3$;

phenyl, optionally substituted with 1, 2, 3, 4, or 5 substituents selected independently from $R^{16}$; and a 3-, 4-, 5-, 6- or 7-membered saturated, partially unsaturated or maximally unsaturated aromatic heterocyclic ring comprising 1, 2, 3 or 4 heteroatoms or heteroatom groups selected from N, O, S, NO, SO and $SO_2$, as ring members, where the heterocyclic ring is optionally substituted with one or more substituents selected independently from $R^{16}$;

or two $R^{11}$ present on the same ring carbon atom of an unsaturated or partially unsaturated heterocyclic ring may together form a group =O, =C($R^{13}$)$_2$, =S;
=S(O)$_m$($R^{15}$)$_2$; =S(O)$_m$$R^{15}$N($R^{14a}$)$R^{14b}$, =$NR^{14}$, =$NOR^{15}$, or =NN($R^{14a}$)$R^{14b}$;

or two $R^{11}$ bound on adjacent ring atoms form together with the ring atoms to which they are bound a saturated 3-, 4-, 5-, 6-, 7-, 8- or 9-membered ring, wherein the ring may contain 1 or 2 heteroatoms or heteroatom groups selected from O, S, N, $NR^{14}$, NO, SO and $SO_2$ and/or 1 or 2 groups selected from C=O, C=S and C=$NR^{14}$ as ring members, and wherein the ring may be substituted by one or more radicals selected from the group consisting of halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{16}$, and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^{16}$;

each $R^{12}$ is independently selected from the group consisting of hydrogen, halogen, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, and phenyl, optionally substituted with 1, 2, 3, 4, or 5 substituents $R^{16}$;

each $R^{13}$ is independently selected from the group consisting of cyano, nitro, —OH, —SH, —SCN, —$SF_5$, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl, $C_3$-$C_8$-cycloalkyl which may be unsubstituted, partially or fully halogenated and/or may carry 1 or 2 radicals selected from $C_1$-$C_4$-alkyl, $C_3$-$C_4$-cycloalkyl, $C_1$-$C_4$-alkoxy, $C_1$-$C_4$-haloalkoxy and oxo; phenyl, benzyl, phenoxy, where the phenyl moiety in the three last-mentioned radicals may be unsubstituted or carry 1, 2, 3, 4 or 5 substituents $R^{16}$; and a 3-, 4-, 5-, 6- or 7-membered saturated, partially unsaturated or maximally unsaturated heterocyclic ring containing 1, 2 or 3 heteroatoms or heteroatom groups selected from N, O, S, NO, SO and $SO_2$, as ring members, where the heterocyclic ring may be substituted by 1, 2 or 3 substituents $R^{16}$;

or two $R^{13}$ present on the same carbon atom of an alkyl, alkenyl, alkynyl or cycloalkyl group may together be =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl); and $R^{13}$ as a substituent on a cycloalkyl ring is additionally selected from the group consisting of $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 substituents selected from CN, $C_3$-$C_4$-cycloalkyl, $C_1$-$C_4$-alkoxy, $C_1$-$C_4$-haloalkoxy and oxo; and $R^{13}$ in the groups =C($R^{13}$)$_2$, —N=C($R^{13}$)$_2$, —C(=O)$R^{13}$, —C(=S)$R^{13}$ and —C(=N$R^{14}$)$R^{13}$ is additionally selected from the group consisting of hydrogen, halogen, $C_1$-$C_6$-alkyl, $C_2$-$C_6$-alkenyl and $C_2$-$C_6$-alkynyl, wherein the three last-mentioned aliphatic radicals may be unsubstituted, partially or fully halogenated and/or may carry 1 or 2 radicals selected from CN, $C_3$-$C_4$-cycloalkyl, $C_1$-$C_4$-alkoxy, $C_1$-$C_4$-haloalkoxy and oxo;

each $R^{14}$ is independently selected from the group consisting of hydrogen, cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from CN, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_4$-cycloalkyl which may be substituted by 1 or 2 substituents selected from halogen and cyano; and oxo;

$C_3$-$C_8$-cycloalkyl which may be unsubstituted, partially or fully halogenated and/or may carry 1 or 2 radicals selected from $C_1$-$C_4$-alkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_3$-$C_4$-cycloalkyl, $C_3$-$C_4$-cycloalkyl-$C_1$-$C_4$-alkyl-, where the cycloalkyl moiety in the two last-mentioned radicals may be substituted by 1 or 2 substituents selected from halogen and cyano; and oxo;

phenyl, benzyl, pyridyl, phenoxy, wherein the cyclic moieties in the four last-mentioned radicals may be unsubstituted and/or carry 1, 2 or 3 substituents selected from halogen, $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl; and a 3-, 4-, 5- or 6-membered saturated, partially unsaturated or maximally unsaturated heterocyclic ring comprising 1 or 2 heteroatoms or heteroatom groups selected from N, O, S, NO, SO and $SO_2$, as ring members, where the heterocyclic ring is optionally substituted with one or more substituents $R^{16}$;

$R^{14a}$ and $R^{14b}$, independently of each other, have one of the meanings given for $R^{14}$; or $R^{14a}$ and $R^{14b}$, together with the nitrogen atom to which they are bound, form a 3-, 4-, 5-, 6- or 7-membered saturated, partially unsaturated or maximally unsaturated heterocyclic ring, wherein the heterocyclic ring may additionally contain 1 or 2 heteroatoms or heteroatom groups selected from N, O, S, NO, SO and $SO_2$, as ring members, where the heterocyclic ring optionally carries one or more substituents selected from halogen, $C_1$-$C_4$-alkyl, $C_1$-$C_4$-haloalkyl, $C_1$-$C_4$-alkoxy and $C_1$-$C_4$-haloalkoxy;

or $R^{14a}$ and $R^{14}$ or $R^{14b}$ and $R^{14}$, together with the nitrogen atoms to which they are bound in the group —C(=N$R^{14}$)N($R^{14a}$)$R^{14b}$, form a 3-, 4-, 5-, 6- or 7-membered partially unsaturated or maximally unsaturated heterocyclic ring, wherein the heterocyclic ring may additionally contain 1 or 2 heteroatoms or heteroatom groups selected from N, O, S, NO, SO and $SO_2$, as ring members, where the heterocyclic ring optionally carries one or more substituents selected from halogen, $C_1$-$C_4$-haloalkyl, $C_1$-$C_4$-alkoxy and $C_1$-$C_4$-haloalkoxy;

each $R^{15}$ is independently selected from the group consisting of hydrogen, cyano, trimethylsilyl, triethylsilyl, tert-butyldimethylsilyl, $C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from $C_3$-$C_4$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo;

$C_3$-$C_8$-cycloalkyl which may be unsubstituted, partially or fully halogenated and/or may carry 1 or 2 radicals selected from $C_1$-$C_4$-alkyl, $C_3$-$C_4$-cycloalkyl, $C_1$-$C_4$- alkoxy, $C_1$-$C_4$-haloalkoxy, $C_1$-$C_4$-alkylthio, $C_1$-$C_4$-alkylsulfinyl, $C_1$-$C_4$-alkylsulfonyl and oxo;

phenyl, benzyl, pyridyl and phenoxy, wherein the four last-mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

each $R^{16}$ is independently selected from the group consisting of halogen, nitro, cyano, —OH, —SH, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, trimethylsilyl, triethylsilyl, tert-butyldimethylsilyl;

$C_1$-$C_6$-alkyl, $C_2$-$C_6$-alkenyl, $C_2$-$C_6$-alkynyl, wherein the three last-mentioned aliphatic radicals may be unsubstituted, partially or fully halogenated and/or may carry 1 or 2 radicals selected from $C_3$-$C_4$-cycloalkyl, $C_1$-$C_4$-alkoxy, $C_1$-$C_4$-haloalkoxy and oxo; $C_3$-$C_8$-cycloalkyl which may be unsubstituted, partially or fully halogenated and/or may carry 1 or 2 radicals selected from $C_1$-$C_4$-alkyl, $C_3$-$C_4$-cycloalkyl, $C_1$-$C_4$-alkoxy, $C_1$-$C_4$-haloalkoxy and oxo;

phenyl, benzyl, pyridyl and phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$-haloalkoxy and ($C_1$-$C_6$-alkoxy)carbonyl;

or two $R^{16}$ present together on the same atom of an unsaturated or partially unsaturated ring may be =O, =S, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

or two $R^{16}$ on two adjacent carbon atoms form together with the carbon atoms they are bonded to a 4-, 5-, 6-, 7- or 8-membered saturated, partially unsaturated or maximally unsaturated ring, wherein the ring may contain 1 or 2 heteroatoms or heteroatom groups selected from N, O, S, NO, SO and $SO_2$, as ring members, and wherein the ring optionally carries one or more substituents selected from halogen, $C_1$-$C_4$-haloalkyl, $C_1$-$C_4$-alkoxy and $C_1$-$C_4$-haloalkoxy;

each n is independently 0, 1 or 2; and
each m is independently 0 or 1;
and the N-oxides, stereoisomers and agriculturally or veterinarily acceptable salts thereof.

In one form, the isothiazoline insecticide is a compound of formula I.1:

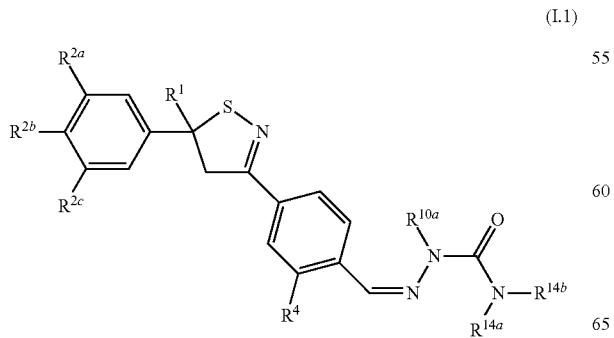

(I.1)

wherein $R^1$ is $C_1$-$C_4$-haloalkyl and is in particular $CF_3$;

$R^{2a}$, $R^{2b}$ and $R^{2c}$ are selected independently from one another from hydrogen, halogen and $C_1$-$C_2$-haloalkyl, preferably from hydrogen, F, Cl, Br and $CF_3$;

$R^4$ is selected from hydrogen, halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, and preferably from hydrogen, F, Cl, Br, $CH_3$, $CF_3$, $OCH_3$, $OCF_2H$, $OCF_3$, $SCH_3$, $SCF_2H$, and $SCF_3$;

$R^{10a}$ and $R^{14a}$ independently from each other are selected from hydrogen, $C_1$-$C_6$-alkyl, $C_1$-$C_6$-haloalkyl, preferably from hydrogen and $CH_3$;

$R^{14b}$ is selected from hydrogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_6$-cycloalkyl, $C_3$-$C_6$-halocycloalkyl, $C_3$-$C_6$-cycloalkyl-$C_1$-$C_4$-alkyl-, where the cycloalkyl moieties in the three last-mentioned groups may be substituted by a cyano group; $C_1$-$C_6$-alkyl substituted with a cyano group, $C_1$-$C_6$-alkoxy, $C_1$-$C_6$-haloalkoxy, phenyl which is optionally substituted with 1, 2, 3 or 4, substituents each independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl; and a heteromonocyclic ring selected from rings of formulae D-1 to D-181

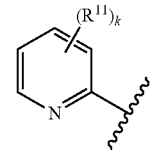

D-1

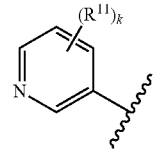

D-2

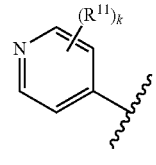

D-3

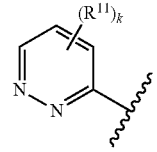

D-4

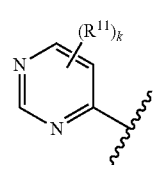

D-5

-continued
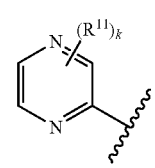 D-6
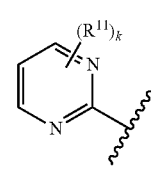 D-7
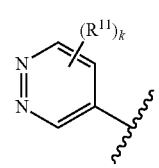 D-8
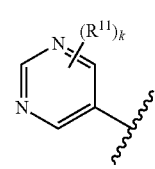 D-9
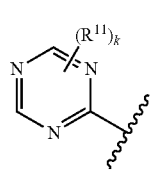 D-10
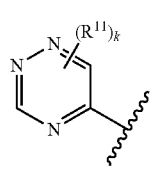 D-11
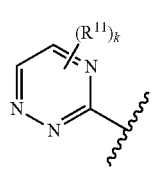 D-12
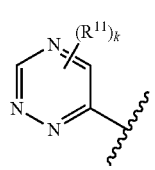 D-13
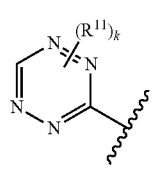 D-14
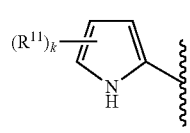 D-15
-continued
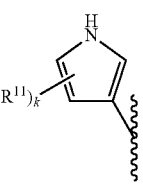 D-16
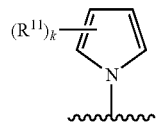 D-17
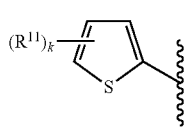 D-18
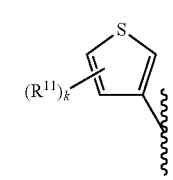 D-19
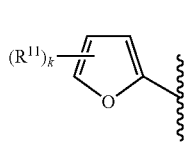 D-20
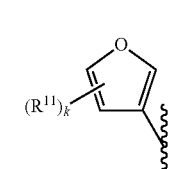 D-21
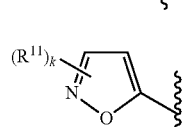 D-22
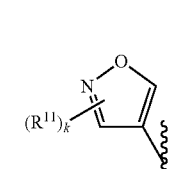 D-23
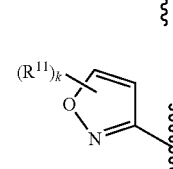 D-24
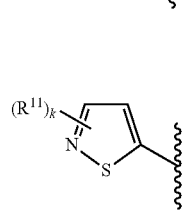 D-25

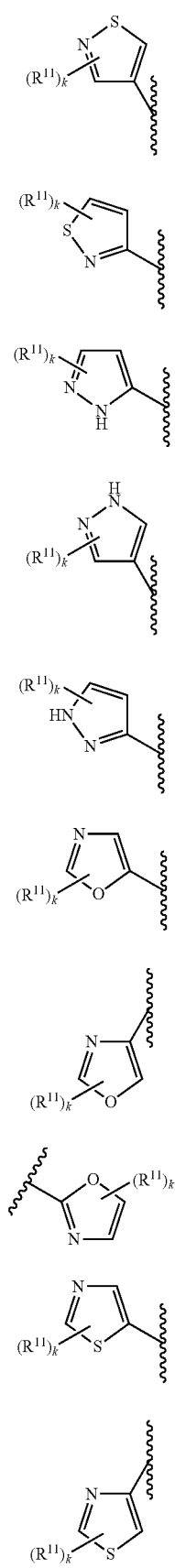
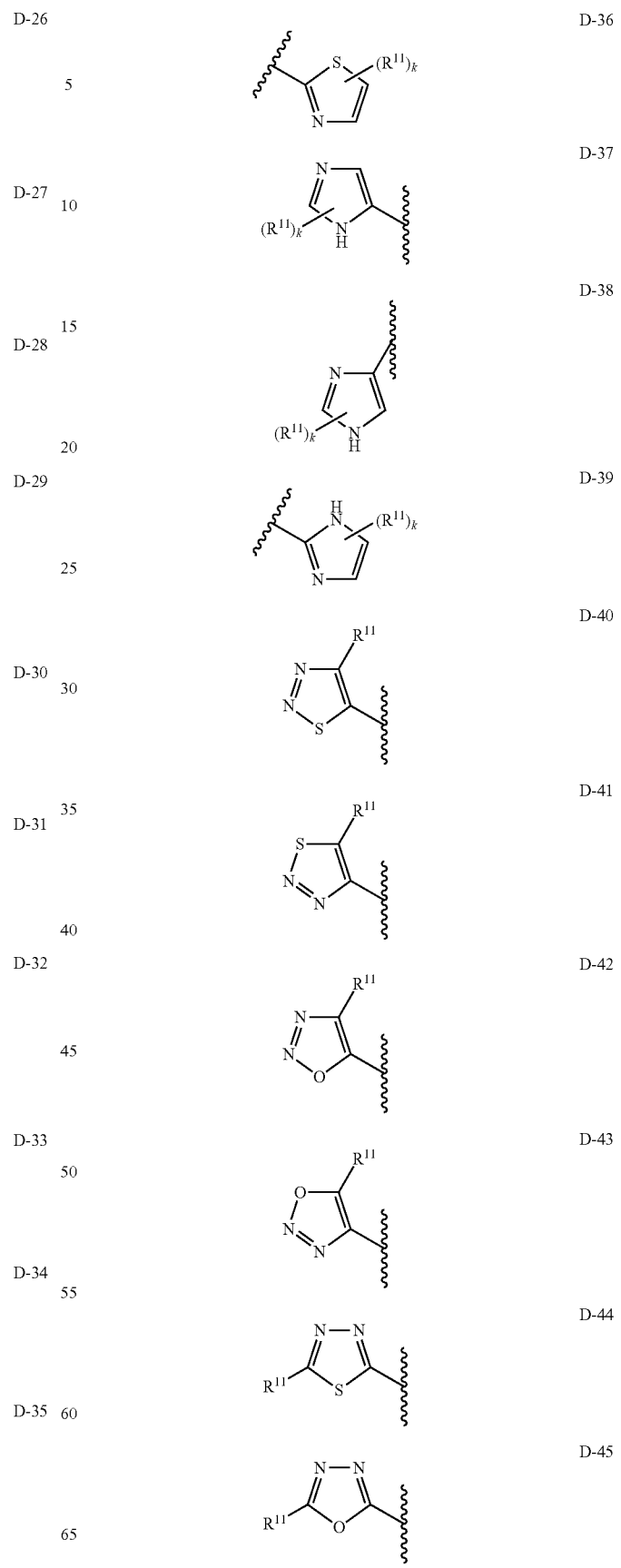
D-26
D-27
D-28
D-29
D-30
D-31
D-32
D-33
D-34
D-35
D-36
D-37
D-38
D-39
D-40
D-41
D-42
D-43
D-44
D-45

-continued
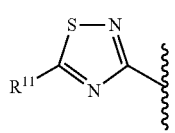 D-46
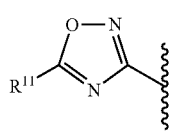 D-47
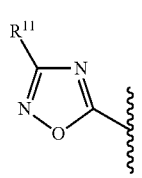 D-48
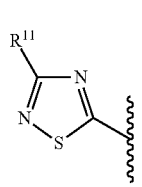 D-49
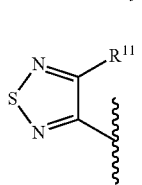 D-50
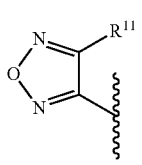 D-51
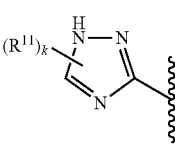 D-52
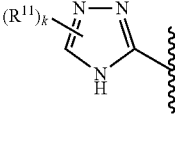 D-53
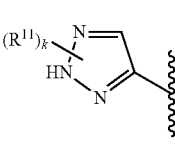 D-54
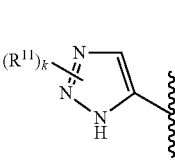 D-55
-continued
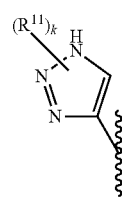 D-56
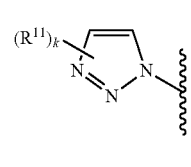 D-57
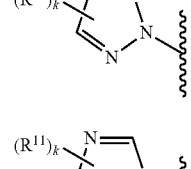 D-58
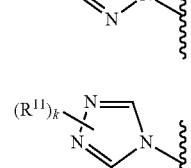 D-59
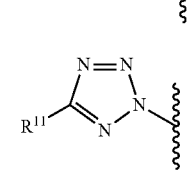 D-60
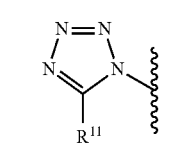 D-61
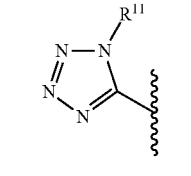 D-62
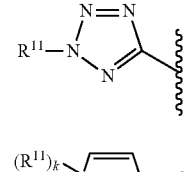 D-63
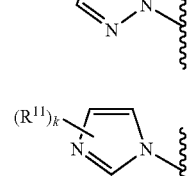 D-64
 D-65
D-66

-continued
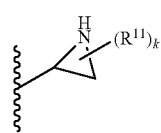 D-67
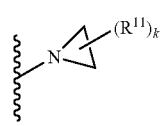 D-68
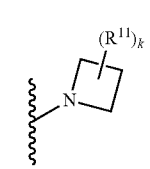 D-69
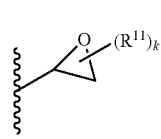 D-70
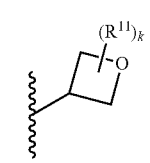 D-71
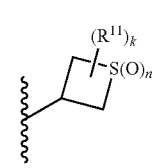 D-72
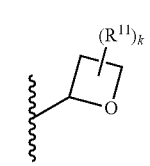 D-73
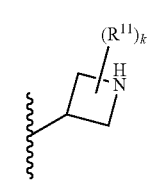 D-74
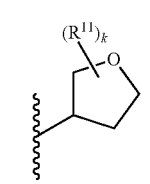 D-75
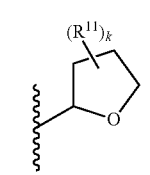 D-76
-continued
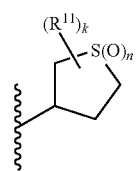 D-77
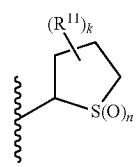 D-78
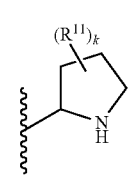 D-79
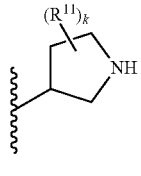 D-80
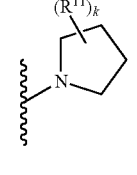 D-81
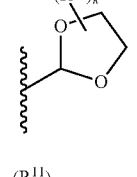 D-82
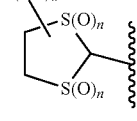 D-83
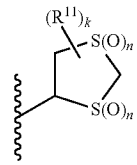 D-84
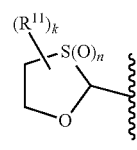 D-85

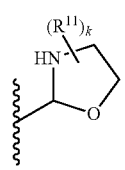 D-86
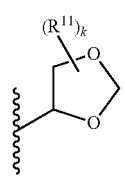 D-87
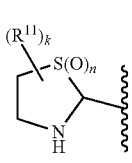 D-88
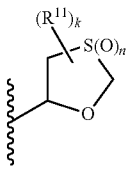 D-89
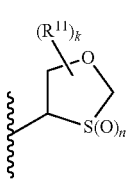 D-90
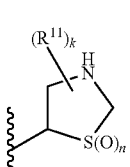 D-91
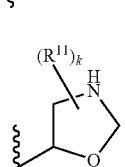 D-92
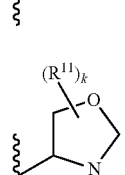 D-93
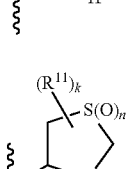 D-94
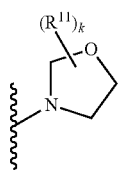 D-95
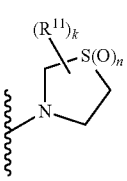 D-96
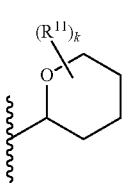 D-97
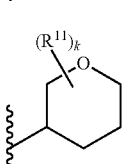 D-98
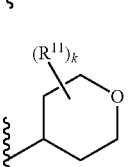 D-99
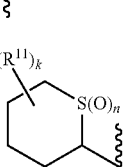 D-100
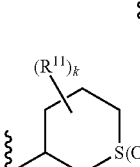 D-101
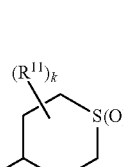 D-102
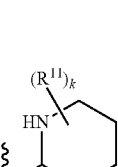 D-103

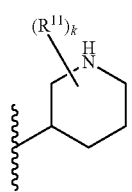 D-104
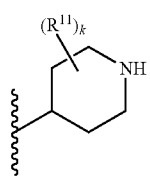 D-105
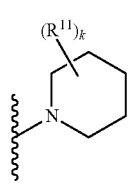 D-106
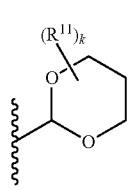 D-107
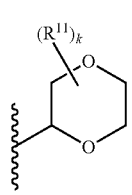 D-108
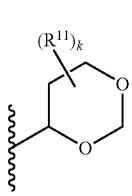 D-109
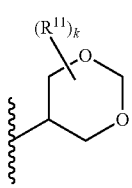 D-110
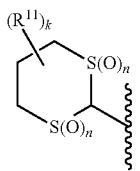 D-111
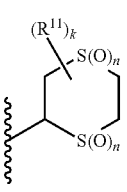 D-112
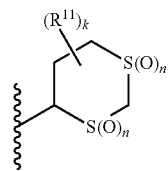 D-113
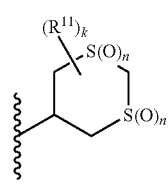 D-114
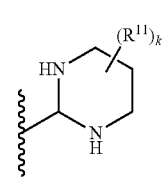 D-115
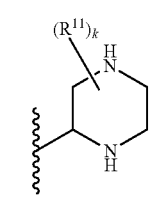 D-116
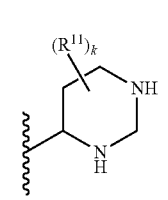 D-117
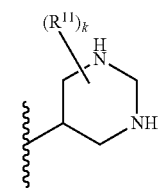 D-118
D-119

-continued
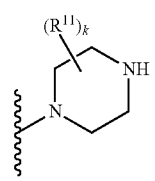 D-120
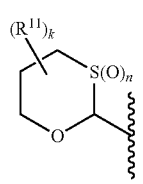 D-121
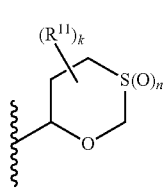 D-122
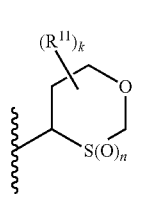 D-123
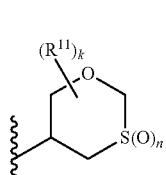 D-124
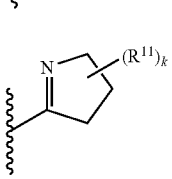 D-125
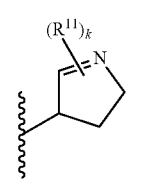 D-126
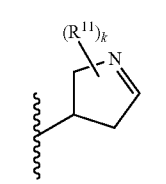 D-127
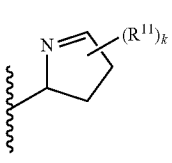 D-128
-continued
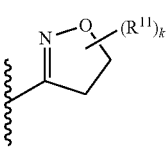 D-129
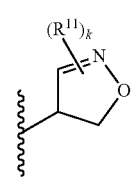 D-130
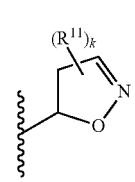 D-131
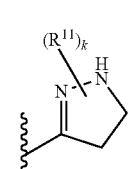 D-132
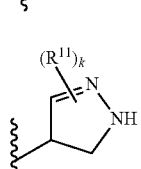 D-133
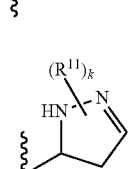 D-134
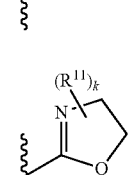 D-135
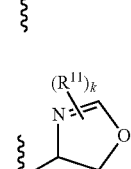 D-136
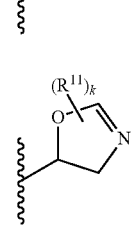 D-137

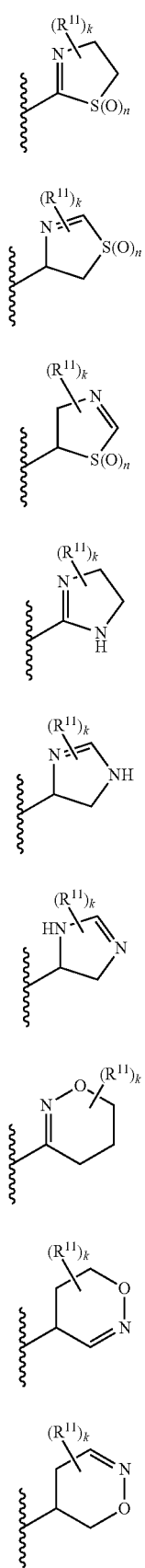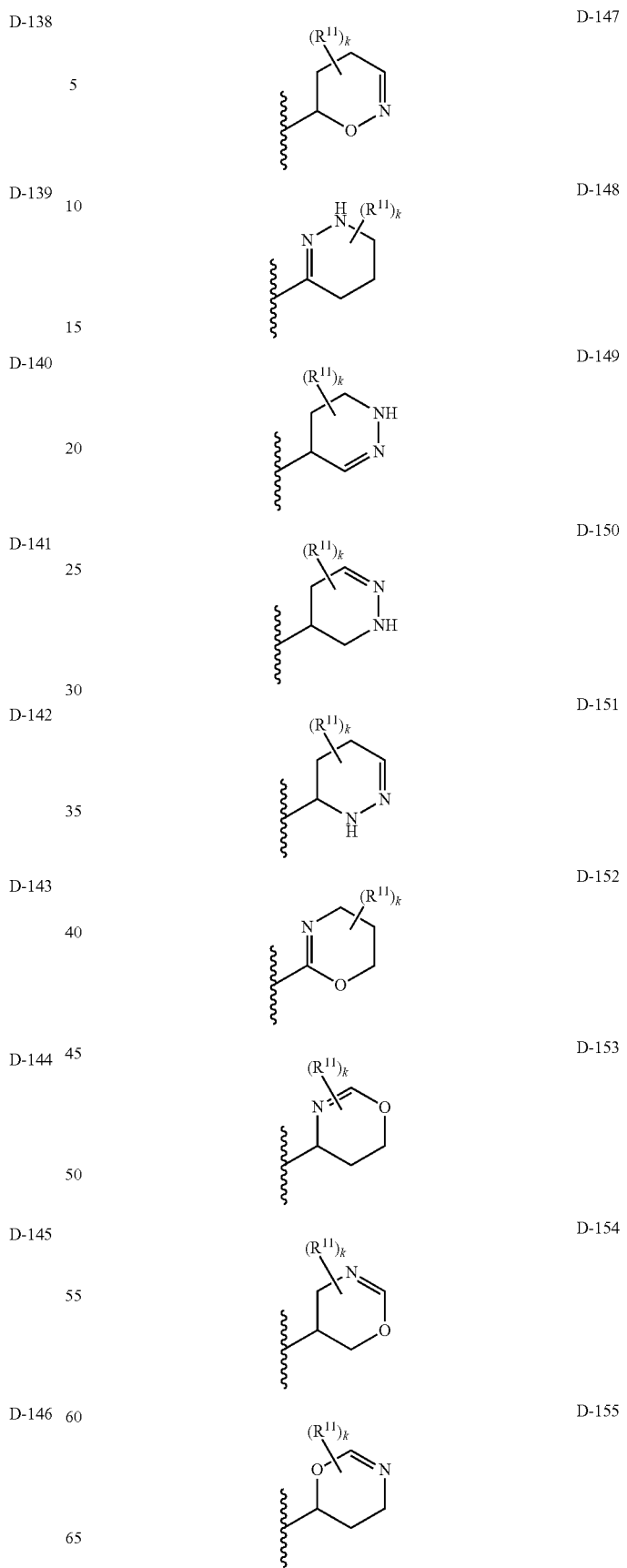

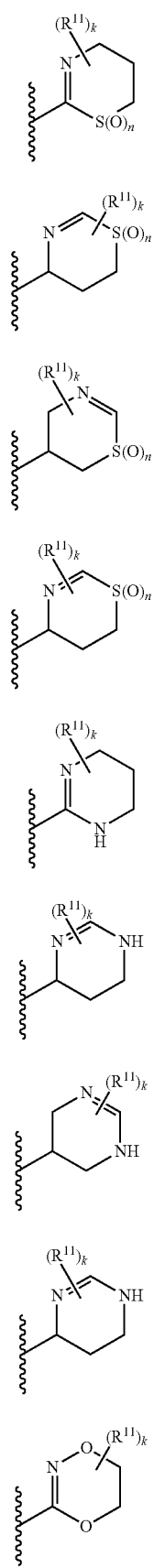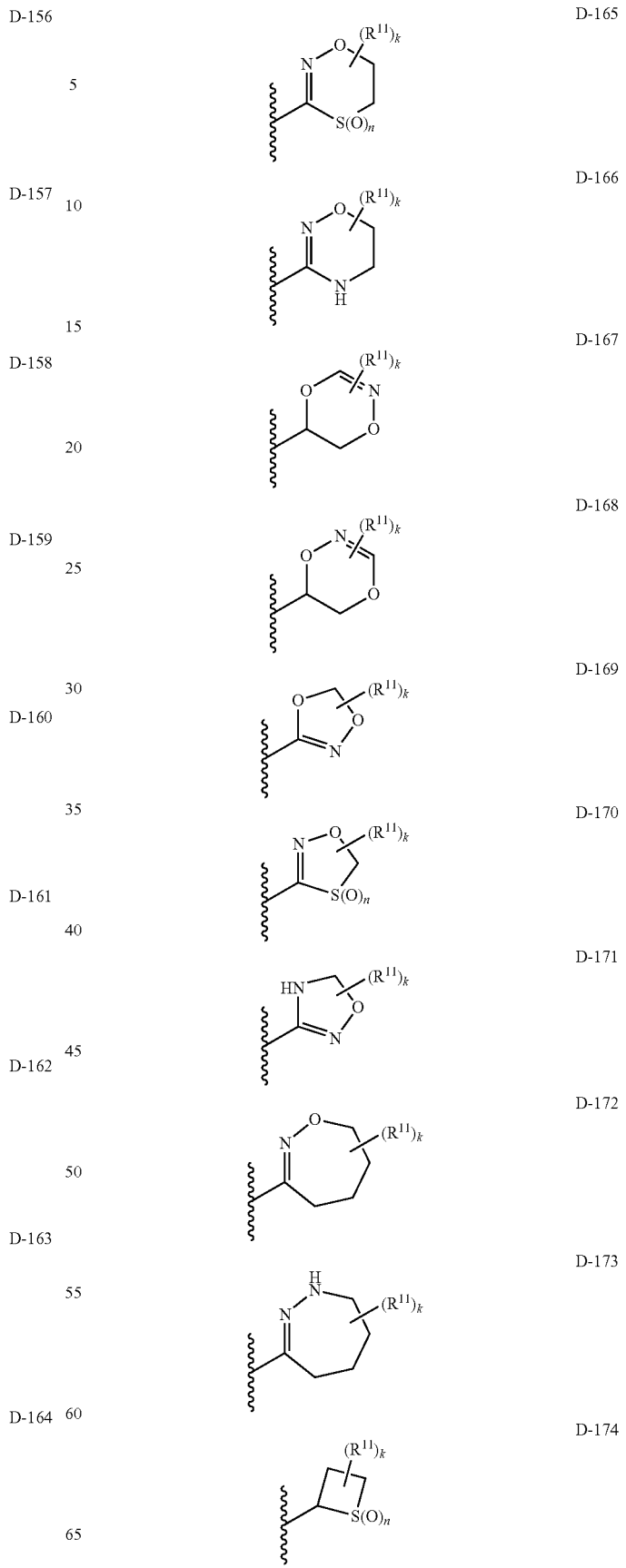

-continued

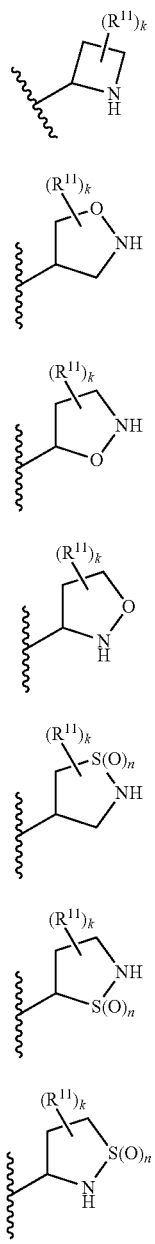

D-175

D-176

D-177

D-178

D-179

D-180

D-181 wherein
k is 0, 1, 2 or 3;
n is 0, 1 or 2; and each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl, $C_1$-$C_4$-alkylcarbonyl, $C_1$-$C_4$-alkylaminocarbonyl, or two $R^{11}$ present on the same carbon atom of a saturated heterocyclic ring may form together =O or =S.

In another form, the isothiazoline insecticide is a compound of formula I.2:

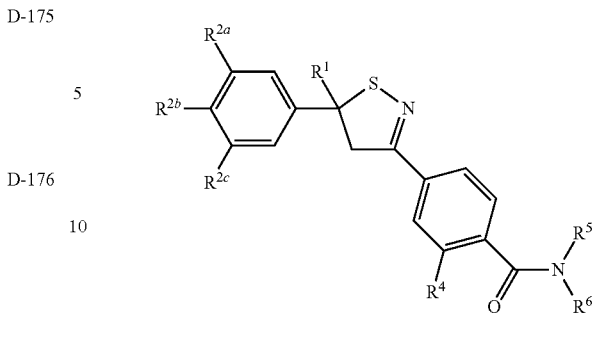

(I.2)

wherein
$R^1$ is $C_1$-$C_4$-haloalkyl and is in particular $CF_3$;
$R^{2a}$, $R^{2b}$ and $R^{2c}$ are selected independently from one another from hydrogen, halogen and $C_1$-$C_2$-haloalkyl, preferably from hydrogen, F, Cl, Br and $CF_3$;
$R^4$ is selected from hydrogen, halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, and preferably from hydrogen, F, Cl, Br, $CH_3$, and $CF_3$;
$R^5$ is selected from hydrogen, $C_1$-$C_6$-alkyl, $C_2$-$C_3$-alkenyl, $C_2$-$C_3$-alkynyl, —$CH_2$—CN and $C_1$-$C_6$-alkoxymethyl-, and preferably from hydrogen and $C_1$-$C_4$-alkyl; and
$R^6$ is selected from hydrogen, $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_6$-haloalkenyl, $C_2$-$C_6$-alkynyl, $C_3$-$C_6$-cycloalkyl which may be substituted by 1 to 4 substituents selected from halogen, cyano; $N(R^{10a})R^{10b}$, —CH=$NOR^9$; phenyl which may be substituted with 1, 2, 3, 4, or 5 substituents $R^{11}$, and a heteromonocyclic ring selected from rings of formulae D-1 to D-181 as defined above;
$R^8$ is selected from hydrogen, OH, CN, $C_3$-$C_8$-cycloalkyl, $C_2$-$C_6$-alkenyl, $C_2$-$C_6$-alkynyl, wherein the three last-mentioned radicals may be partially or fully halogenated and/or may be substituted by one or more cyano group; $C_1$-$C_6$-alkoxy, $C_1$-$C_6$-alkylthio, $C_1$-$C_6$-alkylsulfinyl, $C_1$-$C_6$-alkylsulfonyl, wherein the four last-mentioned radicals may be partially or fully halogenated and/or may be substituted by one or more substituents selected from cyano, $C_3$-$C_6$-cycloalkyl, $C_2$-$C_6$-alkenyl, $C_2$-$C_6$-alkynyl; —C(=O)N($R^{14a}$)$R^{14b}$; phenyl, optionally substituted with 1, 2, 3, 4 or 5 substituents $R^{11}$; and a heteromonocyclic ring selected from rings of formulae D-1 to D-181 as defined above;
$R^9$ is selected from hydrogen, $C_1$-$C_6$-alkyl, $C_3$-$C_6$-cycloalkyl, $C_3$-$C_6$-cycloalkylmethyl, wherein the three last-mentioned radicals may be partially or fully halogenated and/or may be substituted by one or more CN;
$R^{10a}$ is selected from the group consisting of hydrogen and $C_1$-$C_6$-alkyl;
$R^{10b}$ is selected from the group consisting of hydrogen, C(=O)N($R^{14a}$)$R^{14b}$; phenyl, optionally substituted with 1, 2, 3, 4 or 5 substituents $R^{11}$; and a heteromonocyclic ring selected from rings of formulae D-1 to D-181 as defined above;
each $R^{11}$ is independently selected from the group consisting of hydrogen, halogen, cyano, nitro, $C_1$-$C_4$-alkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$- alkynyl and C₂-C₄-haloalkynyl, C₁-C₄-alkylcarbonyl, C₁-C₄-alkylaminocarbonyl; or two R¹¹ present on the same carbon atom of a saturated heterocyclic ring may form together =O or =S;

each $R^{14a}$ is selected from the group consisting of hydrogen and $C_1$-$C_6$-alkyl;

each $R^{14b}$ is selected from the group consisting of hydrogen, $C_1$-$C_6$-alkyl, $C_3$-$C_6$-cycloalkyl, $C_3$-$C_6$-cycloalkylmethyl, $C_2$-$C_4$-alkynyl, $C_2$-$C_4$-alkenyl, $C_1$-$C_4$-alkoxy, wherein the six last-mentioned radicals may be partially or fully halogenated and/or may be substituted with one cyano group.

In yet another form, the isothiazoline insecticide is a compound of formula I.2a:

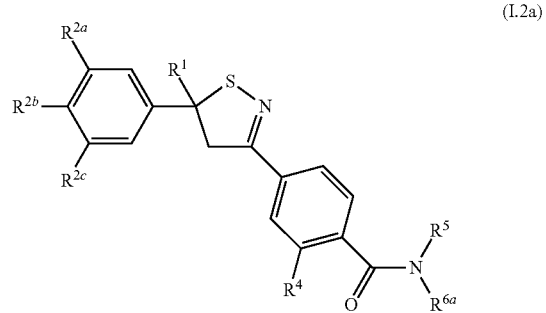

(I.2a)

wherein $R^1$ is $C_1$-$C_4$-haloalkyl and is in particular $CF_3$;

$R^{2a}$, $R^{2b}$ and $R^{2c}$ are selected independently from one another from hydrogen, halogen and $C_1$-$C_2$-haloalkyl, preferably from hydrogen, F, Cl, Br and $CF_3$;

$R^4$ is selected from hydrogen, halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, and preferably from hydrogen, F, Cl, Br, $CH_3$, and $CF_3$;

$R^5$ is selected from hydrogen, $C_1$-$C_6$-alkyl, $C_2$-$C_3$-alkenyl, $C_2$-$C_3$-alkynyl, $CH_2$—CN and $C_1$-$C_6$-alkoxy-methyl-, and preferably from hydrogen and $C_1$-$C_4$-alkyl; and $R^{6a}$ is selected from —X—$R^{6b}$ and —N($R^{5a}$)$R^{6c}$; wherein X is selected from —C($R^a$)₂—, —C($R^a$)₂—C($R^a$)₂—, —C($R^a$)₂—C(=O)—NR$^{10a}$—C($R^a$)₂—, —C($R^a$)₂S(O)ₙ—C($R^a$)₂—, —C($R^a$)₂—C($R^a$)₂—S(O)ₙ—C($R^a$)₂—, —C($R^a$)₂—O—C($R^a$)₂—, and —C($R^a$)₂—C($R^a$)₂—O—C($R^a$)₂—, and preferably from —C($R^a$)₂—, —C($R^a$)₂—C(=O)—NH—C($R^a$)₂—, —C($R^a$)₂—C($R^a$)₂—S(O)₂—C($R^a$)₂—, and —C($R^a$)₂—C($R^a$)₂—O—C($R^a$)₂—, wherein n is 0, 1 or 2, and each $R^a$ is independently selected from the group consisting of hydrogen, halogen, $C_1$-$C_3$-alkyl, and $C_1$-$C_3$-haloalkyl and is preferably hydrogen;

$R^{5a}$ is selected from hydrogen, and $C_1$-$C_6$-alkyl, and is preferably hydrogen;

$R^{6b}$ is selected from the group consisting of $C_3$-$C_6$-cycloalkyl, $C_2$-$C_6$-alkenyl, $C_2$-$C_6$-alkynyl, wherein the three last-mentioned radicals may be partially or fully halogenated and/or may be substituted by one or more substituents $R^8$;

$R^{6c}$ is —C(=O)N($R^{14a}$)$R^{14b}$ $R^8$ is selected from, cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{14a}$)$R^{14b}$;

each $R^{14a}$ is selected from the group consisting of hydrogen and $C_1$-$C_6$-alkyl;

each $R^{14b}$ is selected from the group consisting of hydrogen, $C_1$-$C_6$-alkyl, $C_3$-$C_6$-cycloalkyl, $C_3$-$C_6$-cycloalkylmethyl, $C_2$-$C_4$-alkynyl, $C_2$-$C_4$-alkenyl, $C_1$-$C_4$-alkoxy, wherein the six last-mentioned radicals may be partially or fully halogenated and/or may be substituted with one cyano group;

where in case that $R^5$ is hydrogen, $R^{6a}$ is further selected from hydrogen, 1-cyanocyclopropyl, 1-cyanocyclobutyl and 1-cyanocyclopentyl.

In another form, the isothiazoline insecticide is a compound of formula I.3:

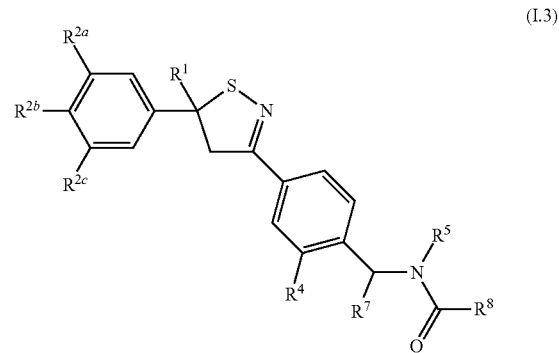

(I.3)

wherein $R^1$ is $C_1$-$C_4$-haloalkyl and is in particular $CF_3$;

$R^{2a}$, $R^{2b}$ and $R^{2c}$ are selected independently from one another from hydrogen, halogen and $C_1$-$C_2$-haloalkyl, preferably from hydrogen, F, Cl, Br and $CF_3$;

$R^4$ is selected from hydrogen, halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio, and preferably from hydrogen, F, Cl, Br, $CH_3$, $CF_3$, $OCH_3$, $OCF_3$, $OCF_2H$, $OCF_3$, $SCH_3$, $SCF_2H$, and $SCF_3$;

$R^5$ is selected from hydrogen, $C_1$-$C_4$-alkyl, $C_2$-$C_3$-alkynyl, —$CH_2$—CN and $C_1$-$C_6$-alkoxy-methyl-, and preferably from hydrogen and $C_1$-$C_4$-alkyl;

$R^7$ is hydrogen or methyl;

$R^8$ is selected from the group consisting of hydrogen, $C_1$-$C_6$-alkyl, $C_3$-$C_6$-cycloalkyl, $C_3$-$C_6$-alkenyl, wherein the three last-mentioned radicals may be partially or fully halogenated and/or may be substituted by one or more substituents $R^{13}$; $C_3$-$C_8$-alkynyl, —N($R^{10a}$)$R^{10b}$, —C(=O)N($R^{14a}$)$R^{14b}$, —CH=NOR⁹; phenyl, optionally substituted with 1, 2, 3, 4 or 5 substituents $R^{11}$; and a heterocyclic ring selected from rings of formulae D-1 to D-181 as defined above;

$R^9$ is selected from hydrogen, $C_1$-$C_6$-alkyl, $C_3$-$C_6$-cycloalkyl, $C_3$-$C_6$-cycloalkylmethyl, wherein the three last-mentioned radicals may be partially or fully halogenated and/or may be substituted by one or more cyano group;

$R^{10a}$ is selected from the group consisting of hydrogen and $C_1$-$C_6$-alkyl;

$R^{10b}$ is selected from the group consisting of hydrogen, $C_1$-$C_6$-alkyl, $C_1$-$C_6$-cycloalkyl, wherein the two last-mentioned radicals may be partially or fully halogenated and/or are optionally substituted by one cyano group; —C(=O)N($R^{14a}$)$R^{14b}$; phenyl, optionally substituted with 1, 2, 3, 4 or 5 substituents $R^{11}$; and a heteromonocyclic ring selected from rings of formulae D-1 to D-181 as defined above;

each $R^{11}$ is independently selected from the group consisting of hydrogen, halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl, $C_1$-$C_4$-alkylcarbonyl, $C_1$-$C_4$-alkylaminocarbonyl; or two $R^{11}$ present on the same carbon atom of a saturated heterocyclic ring may form together =O or =S;

$R^{13}$ is selected from cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{14a}$)$R^{14b}$, phenyl, optionally substituted with 1, 2, 3, 4 or 5 substituents $R^{11}$ and a heterocyclic ring selected from rings of formulae D-1 to D-181 as defined above; and is preferably selected from $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfonyl and $C_1$-$C_6$-haloalkylsulfonyl;

each $R^{14a}$ is selected from the group consisting of hydrogen and $C_1$-$C_6$-alkyl; and each $R^{14b}$ is selected from the group consisting of hydrogen, $C_1$-$C_6$-alkyl, $C_2$-$C_4$-alkynyl, $C_2$-$C_4$-alkenyl, —CH$_2$—CN, $C_1$-$C_6$-haloalkyl, $C_3$-$C_6$-cycloalkyl, $C_3$-$C_6$-halocycloalkyl, $C_1$-$C_4$-alkoxy and $C_1$-$C_4$-haloalkoxy, $C_3$-$C_6$-cycloalkylmethyl.

In another form, the isothiazoline insecticide is a compound of formula I.4:

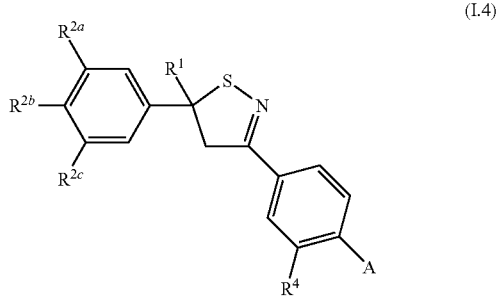

(I.4)

wherein $R^1$ is $C_1$-$C_4$-haloalkyl and is in particular $CF_3$;

$R^{2a}$, $R^{2b}$ and $R^{2c}$ are selected independently from one another from hydrogen, halogen and $C_1$-$C_2$-haloalkyl, preferably from hydrogen, F, Cl, Br and $CF_3$;

$R^4$ is selected from hydrogen, halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio; and A is $A^4$ and selected from rings of formulae D-1 to D-181 as defined above, preferably selected from D-59, D-65 and D-66 and in particular D-59.

Activated charcoal is well known in the art (see for example: Henning et al. Carbon, 5. Activated Carbon. Ullmann's Encyclopedia of Industrial Chemistry, Vol. 6, pp. 771-796, 2012. DOI: 10.1002/14356007.n5_n04). Activated charcoal is a microcrystalline, non-graphite form of carbon, which has been processed to develop an increased surface area and pore volume. The activated charcoal can form a complex with the insecticide of the present invention, including entrapment of the insecticide within its pores.

Activated charcoal may be present in a range of 1-40 wt %, preferably 5-35 wt %, and in particular 10-25 wt %.

The preferred activated carbon particle mesh size range is 80% through 100 mesh (≤150 um), and 50% through 325 mesh (≤45 um). The more preferred activated carbon particle size is 90% through 100 mesh and 60% through 325 mesh. The most preferred particle size range is 99% through 100 mesh and 70% through 325 mesh. The particle size of the activated charcoal used in the invention may be reduced by air milling down to d50 of 20 to 50 □m prior to wet milling with the active ingredient and inert ingredients.

It is well documented that activated charcoal is able to deactivate pesticides (Jordan and Smith, Weed Source, Volume 19, Issue 5 (September 71), ppg. 541-544 and WO 97/04864). Surprising, it has been found that in the suspension concentrate composition disclosed herein, the isothiazoline insecticide is not deactivated.

The suspension concentrate disclosed herein may also further comprise pesticides. The term pesticides refer to at least one active substance selected from the group of the fungicides, insecticides, nematicides, herbicides, safeners and/or growth regulators. Preferred pesticides are fungicides, insecticides, herbicides and growth regulators. Especially preferred pesticides are fungicides. Mixtures of pesticides from two or more of the abovementioned classes may also be used. The skilled worker is familiar with such pesticides, which can be found, for example, in Pesticide Manual, 15th Ed. (2009), The British Crop Protection Council, London, the entire contents of which are hereby incorporated by reference. The following pesticides are suitable, by way of example (pesticides A) to K) are fungicides):

A) Respiration Inhibitors

Inhibitors of complex III at $Q_o$ site (e.g. strobilurins): azoxystrobin, coumethoxystrobin, coumoxystrobin, dimoxystrobin, enestroburin, fenaminstrobin, fenoxystrobin/flufenoxystrobin, fluoxastrobin, kresoxim-methyl, metominostrobin, orysastrobin, picoxystrobin, pyraclostrobin, pyrametostrobin, pyraoxystrobin, trifloxystrobin, 2-[2-(2,5-dimethyl-phenoxymethyl)-phenyl]-3-methoxy-acrylic acid methyl ester and 2-(2-(3-(2,6-dichlorophenyl)-1-methyl-allylideneaminooxymethyl)-phenyl)-2-methoxyimino-N-methyl-acetamide, pyribencarb, triclopyricarb/chlorodincarb, famoxadone, fenamidone;

inhibitors of complex III at $Q_i$ site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S, 7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3S,6S, 7R,8R)-3-[[(3-hydroxy-4-methoxy-2-pyridinyl) carbonyl]amino]-6-methyl-4,9-dioxo-8-(phenylmethyl)-1,5-dioxonan-7-yl2-methylpropanoate inhibitors of complex II (e. g. carboxamides): benodanil, benzovindiflupyr, bixafen, boscalid, carboxin, fenfuram, fluopyram, flutolanil, fluxapyroxad, furametpyr, isopyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3-(trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 3-(difluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide;

other respiration inhibitors (e.g. complex I, uncouplers): diflumetorim, (5,8-difluoroquinazolin-4-yl)-{2-[2-fluoro-4-(4-trifluoromethylpyridin-2-yloxy)-phenyl]ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol Biosynthesis Inhibitors (SBI Fungicides)
C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranylmethyl]-2H[1,2,4]triazole-3-thiol;
imidazoles: imazalil, pefurazoate, prochloraz, triflumizol; pyrimidines, pyridines and piperazines: fenarimol, nuarimol, pyrifenox, triforine;
Delta14-reductase inhibitors: aldimorph, dodemorph, dodemorph-acetate, fenpropimorph, tridemorph, fenpropidin, piperalin, spiroxamine;
Inhibitors of 3-keto reductase: fenhexamid;

C) Nucleic Acid Synthesis Inhibitors
phenylamides or acyl amino acid fungicides: benalaxyl, benalaxyl-M, kiralaxyl, metalaxyl, metalaxyl-M (mefenoxam), ofurace, oxadixyl;
others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4-amine;

D) Inhibitors of Cell Division and Cytoskeleton
tubulin inhibitors, such as benzimidazoles, thiophanates: benomyl, carbendazim, fuberidazole, thiabendazole, thiophanate-methyl; triazolopyrimidines: 5-chloro-7-(4-methylpiperidin-1-yl)-6-(2,4,6-trifluorophenyl)-[1,2,4]triazolo[1,5-a]pyrimidine
other cell division inhibitors: diethofencarb, ethaboxam, pencycuron, fluopicolide, zoxamide, metrafenone, pyriofenone;

E) Inhibitors of Amino Acid and Protein Synthesis
methionine synthesis inhibitors (anilino-pyrimidines): cyprodinil, mepanipyrim, pyrimethanil;

protein synthesis inhibitors: blasticidin-S, kasugamycin, kasugamycin hydrochloride-hydrate, mildiomycin, streptomycin, oxytetracyclin, polyoxine, validamycin A;

F) Signal Transduction Inhibitors
MAP/histidine kinase inhibitors: fluoroimid, iprodione, procymidone, vinclozolin, fenpiclonil, fludioxonil;
G protein inhibitors: quinoxyfen;

G) Lipid and Membrane Synthesis Inhibitors
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl)-ethanesulfonyl)-but-2-yl) carbamic acid-(4-fluorophenyl) ester;
compounds affecting cell membrane permeability and fatty acides: propamocarb, propamocarb-hydrochlorid;
fatty acid amide hydrolase inhibitors: oxathiapiprolin;

H) Inhibitors with Multi-Site Action
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e.g. phthalimides, sulfamides, chloronitriles): anilazine, chlorothalonil, captafol, captan, folpet, dichlofluanid, dichlorophen, flusulfamide, hexachlorobenzene, pentachlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H[1,4]dithiino[2,3-c:5,6-c']dipyrrole-1,3,5,7(2H,6H)-tetraone;

I) Cell Wall Synthesis Inhibitors
inhibitors of glucan synthesis: validamycin, polyoxin B;
melanin synthesis inhibitors: pyroquilon, tricyclazole, carpropamid, dicyclomet, fenoxanil;

J) Plant Defense Inducers
acibenzolar-S-methyl, probenazole, isotianil, tiadinil, prohexadione-calcium; phosphonates:
fosetyl, fosetyl-aluminum, phosphorous acid and its salts;

K) Unknown Mode of Action
bronopol, chinomethionat, cyflufenamid, cymoxanil, dazomet, debacarb, diclomezine, difenzoquat, difenzoquat-methylsulfate, diphenylamin, fenpyrazamine, flumetover, flusulfamide, flutianil, methasulfocarb, nitrapyrin, nitrothal-isopropyl, oxathiapiprolin, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, oxin-copper, proquinazid, tebufloquin, tecloftalam, triazoxide, 2-butoxy-6-iodo-3-propylchromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N-methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, 2methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chloro-phenyl)-2,3-dimethyl-isoxazolidin-3-yl]pyridine (pyrisoxazole), N-(6-methoxy-pyridin-3-yl)cyclopropanecarboxylic acid amide, 5-chloro-1-(4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide;

M) Growth Regulators abscisic acid, amidochlor, ancymidol, 6-benzylaminopurine, brassinolide, butralin, chlormequat (chlormequat chloride), choline chloride, cyclanilide, daminozide, dikegulac, dimethipin, 2,6-dimethylpuridine, ethephon, flumetralin, flurprimidol, fluthiacet, forchlorfenuron, gibberellic acid, inabenfide, indole-3-acetic acid, maleic hydrazide, mefluidide, mepiquat (mepiquat chloride), naphthaleneacetic acid, N-6-benzyladenine, paclobutrazol, prohexadione (prohexadione-calcium), prohydrojasmon, thidiazuron, triapenthenol, tributyl phosphorotrithioate, 2,3,5-tri-iodobenzoic acid, trinexapac-ethyl and uniconazole;

N) Insecticides organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1-2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide; macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

ryanodine receptor inhibitors: chlorantraniliprole, cyantraniliprole, flubendiamide, N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-methyl-phenyl]-2-(3-chloro-2-pyridyl)-5-(trifluoromethyl)pyrazole-3-carboxamide; N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide; N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-cyano-phenyl]-2-(3-chloro-2-pyridyl)-5-(trifluoromethyl)pyrazole-3-carboxamide; N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide;

others: benclothiaz, bifenazate, cartap, flonicamid, pyridalyl, pymetrozine, sulfur, thiocyclam, cyenopyrafen, flupyrazofos, cyflumetofen, amidoflumet, imicyafos, bistrifluron, pyrifluquinazon and 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl] cyclopropaneacetic acid ester.

The pesticide can have a melting point of more than 50° C., preferably more than 70° C. and in particular more than 90° C.

The pesticide is preferably present in the suspension concentrate composition as a complex with the activated charcoal particles or suspended in the solution. These particles may have a d(50) of 0.5 to 10 µm, preferably 2 to 5 µm. It is not excluded that some crystals of active ingredient are suspended in the suspension concentrate while some form a complex with the activated charcoal. These crystals may have a d(50) of 0.5 to 10 µm, preferably 2 to 5 µm.

The suspension concentrate composition can furthermore comprise auxiliaries conventionally used for crop protection products. Suitable auxiliaries are liquid carriers, surfactants, dispersants, emulsifiers, wetters, adjuvants, solubilizers, penetrants, protective colloids, stickers, thickeners, bactericides, antifreeze agents, antifoam agents, colorants, adhesives and binders.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetrant, protective colloid, or auxiliary. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-subsititued fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate. Preferred nonionic surfactants are alkoxylates. Nonionic surfactants such as alkoxylates may also be employed as adjuvants.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds which have negligible or even no pesticidal activity themselves, and which improve the biological performance of the compound I on the target. Examples are surfactants, mineral or vegetable oils, and other auxilaries. Further examples are listed by Knowles, Adjuvants and Additives, Agrow Reports DS256, T&F Informa UK, 2006, chapter 5.

Suitable bactericides are bronopol and isothiazolinone derivatives such as alkylisothiazolinones and benzisothiazolinones. Suitable antifreeze agents are ethylene glycol, propylene glycol, urea and glycerol. Suitable antifoam agents are silicones, long-chain alcohols, and salts of fatty acids. Suitable colorants (e.g. in red, blue, or green) are pigments which are sparingly soluble in water, and water-soluble dyes. Examples are inorganic colorants (e.g. iron oxide, titanium oxide, iron hexacyanoferrate) and organic colorants (e.g. alizarin, azo and phthalocyanine colorants).

The suspension concentrate composition preferably comprises at least one anionic surfactant. The suspension concentrate composition usually comprises not less than 0.5% by weight of anionic surfactants, preferably not less than 2% by weight and in particular not less than 3% by weight. The suspension concentrate composition can comprise not more than 30% by weight of anionic surfactants, preferably not more than 20% by weight and in particular not more than 15% by weight.

The suspension concentrate composition preferably comprises at least one nonionic surfactant. The suspension concentrate composition usually comprises not less than 1% by weight of nonionic surfactants, preferably not less than 2% by weight and in particular not less than 3% by weight. The suspension concentrate composition can comprise not more than 65% by weight of nonionic surfactants, preferably not more than 45% by weight and in particular not more than 35% by weight.

Preferably, the suspension concentrate composition comprises a nonionic surfactant and an anionic surfactant.

The invention furthermore relates to a process for the preparation of the suspension concentrate composition according to the invention by mixing, via a wet-milling process, the isothiazoline insecticide and activated charcoal which are milled at 5-50° C., until particle size of charcoal or of pesticide d50 between 1 to 5 µm, preferably 2 to 3 µm.

The particle size of the activated charcoal used in the invention may be reduced down to 20 to 50 µm via air milling prior to the wet milling process with the isothiazoline insecticide.

The invention furthermore relates to a suspension obtainable (preferably obtained) by mixing water, and the components a) isothiazoline insecticide and b) activated charcoal according to the invention. The mixing ratio of water to concentrate can be in the range of from 1000 to 1 up to 1 to 1, preferably 200 to 1 up to 3 to 1.

The invention furthermore relates to a method for controlling undesired attack by insects or mites, where the suspension concentrate composition according to the invention or the solution according to the invention is allowed to act on the respective pests, their environment or on the crop plants to be protected from the respective pests. In general, the therapeutic treatment of humans and animals is excluded from the method for controlling undesired attack by insects or mites.

When employed in crop protection, the application rates of the insecticides or pesticides amount to from 0.001 to 2 kg per ha, preferably from 0.005 to 2 kg per ha, especially preferably from 0.05 to 0.9 kg per ha and in particular from 0.1 to 0.75 kg per ha, depending on the nature of the desired effect. In treatment of plant propagation materials such as seeds, e. g. by dusting, coating or drenching seed, amounts of active substance of from 0.1 to 1000 g, preferably from 1 to 1000 g, more preferably from 1 to 100 g and most preferably from 5 to 100 g, per 100 kg of plant propagation material (preferably seed) are generally required. When used in the protection of materials or stored products, the amount of active substance applied depends on the kind of application area and on the desired effect. Amounts customarily applied in the protection of materials are 0.001 g to 2 kg, preferably 0.005 g to 1 kg, of active substance per cubic meter of treated material.

Various types of oils, wetters, adjuvants, fertilizers or micronutrients and further pesticides (for example herbicides, insecticides, fungicides, growth regulators, safeners) may be added to the suspension concentrate composition in the form of a premix or optionally only shortly before use (tank mix). These agents can be admixed to the compositions according to the invention at a weight ratio of from 1:100 to 100:1, preferably from 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

Advantages of the present invention are, inter alia, that the composition is highly stable and remains efficacious after exposure to ultraviolet radiation.

The examples which follow illustrate the invention without imposing any limitation.

EXAMPLES

Example 1: Preparation of Formulations for Testing

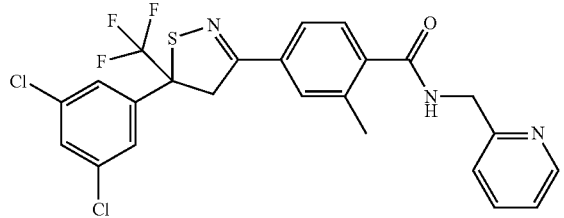 [SMILES: Cc1cc(C2=NSC(c3cc(Cl)cc(Cl)c3)(C(F)(F)F)C2)ccc1C(=O)NCc1ccccn1]

Compound 1: 4-[5-(3,5-dichlorophenyl)-5-(trifluoromethyl)-4H-isothiazol-3-yl]-2-methyl-N-(2-pyridylmethyl)benzamide

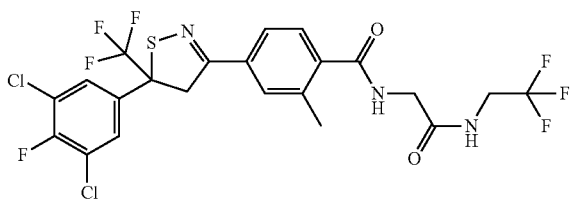 [SMILES: Cc1cc(C2=NSC(c3cc(Cl)c(F)c(Cl)c3)(C(F)(F)F)C2)ccc1C(=O)NCC(=O)NCC(F)(F)F]

Compound 2: 4-[5-(3,5-dichloro-4-fluoro-phenyl)-5-(trifluoromethyl)-4H-isothiazol-3-yl]-2-methyl-N-[2-oxo-2-(2,2,2-trifluoroethylamino)ethyl]benzamide

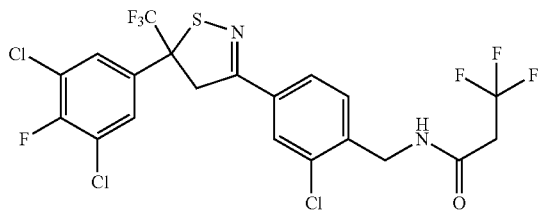 [SMILES: O=C(CC(F)(F)F)NCc1ccc(C2=NSC(c3cc(Cl)c(F)c(Cl)c3)(C(F)(F)F)C2)cc1Cl]

Compound 3: N-[[2-chloro-4-[5-(3,5-dichloro-4-fluoro-phenyl)-5-(trifluoromethyl)-4H-isothiazol-3-yl]phenyl]methyl]-3,3,3-trifluoro-propanamide

| | |
|---|---|
| A | Anionic surfactant: sodium salt of naphthalene sulfonate condensate |
| B | Anionic surfactant: calcium dodecylbenzene sulfonate (branched) in 2-ethylhexanol and propylenglycol |
| C | Surfactant: Non ionic Alkoxylated castor oil |
| D | Surfactant: Non ionic Polyalkylene glycol ether, HLB 17 |
| E | Antifoam: Silicon fluid antifoam agent |
| F | Thickener: Xanthan gum solution, 3% in Water |
| G | Bactericide: mixture of 1,2 benzisothiazolin-3-one and 2 Methyl-4-isothiazoline 3-one |
| H | Anionic Surfactant: calcium dodecylbenzenesulfonate |
| I | Anionic surfactant: Sodium Salt of maleic acid/diisobutylene copolymer |
| L | Thickener: Xanthan gum granules |

Formulation 1: Activated Charcoal Suspension Concentrate (SC), Compound 1.

0.40 g of compound 1, 2 g of activated charcoal (Specific Gravity: 2.3 g/cc real density and particle size 5.5 μm), 0.35 g of surfactant D, 0.35 g of surfactant A, 0.04 g of Antifoam E, 5.48 g of water were weighted into a vessel. 10 ml of glass bead (06-08 mm) were added and an aqueous isothiazoline-charcoal suspension was prepared by using a laboratory disperser (IKA® Ultra Turrax Tube disperser at 3000 rpm, 60 minutes). The suspension was stabilized by addition of 1.33 g thickener F. Moreover, 0.04 g of bactericide G was added to the mixture. The mixture was further shaken for 5 minutes at 3000 rpm. Thereafter the glass beads were filtered off. The particle size was measured via using a particle size analyzer (Malvern) and was found to be: 2.90 μm (d50).

Formulation 2: Reference Example: Emulsifiable Concentrate (EC), Compound 1.

0.8 g of compound 1, 0.48 g of surfactant C, 0.72 g of surfactant A were dissolved in a homogeneous mixture of 1.20 g of heavy aromatic naphtha and 4.8 g of C8/C10 fatty acid dimethylamide. The mixture was stirred at room temperature for 2 hrs in order to ensure homogenization of the sample.

Formulation 3: Activated Charcoal Suspension Concentrate (SC), Compound 2.

0.40 g of compound 2, 2.00 g of activated charcoal (Specific Gravity: 2.3 g/cc real density and particle size 5.5 μm), 0.35 g of surfactant D, 0.35 g of surfactant A, 0.04 g of Antifoam E, 5.48 g of water were weighted into a vessel. 10 ml of glass bead (06-08 mm) were added and an aqueous isothiazoline-charcoal suspension was prepared by prepared by using a laboratory disperser (IKA® Ultra Turrax Tube disperser at 3000 rpm, 45 minutes). The suspension was stabilized by addition of 1.33 g thickener F. Moreover, 0.04 g of bactericide G was added to the mixture. The mixture was further shaken for 5 minutes at 3000 rpm. Thereafter the glass beads were filtered off. The particle size was measured via using a particle size analyzer (Malvern) and was found to be: 3.13 μm (d50).

Formulation 4: Activated Charcoal Suspension Concentrate (SC), Compound 2.

0.40 g of compound 2, 2.00 g of activated charcoal (Specific Gravity: 2.3 g/cc real density and particle size 5.5 μm), 0.10 g of surfactant H, 1.00 g of surfactant I, 0.04 g of antifoam E and 6.38 g of water were weighted into a vessel. 10 ml of glass bead (06-08 mm) were added and an aqueous isothiazoline-charcoal suspension was prepared by prepared by using a laboratory disperser (IKA® Ultra Turrax Tube disperser at 3000 rpm, 45 minutes). The suspension was stabilized by addition of 0.04 g thickener L. Moreover, 0.04 g of bactericide G was added to the mixture. The mixture was further shaken for 5 minutes at 3000 rpm. Thereafter the glass beads were filtered off. The particle size was measured via using a particle size analyzer (Malvern) and was found to be: 2.75 μm (d50).

Formulation 5: Activated Charcoal Suspension Concentrate (SC), Compound 3.

0.40 g of compound 3, 2.0 g of activated charcoal (Specific Gravity: 2.3 g/cc real density and particle size 5.5 μm), 0.35 g of surfactant D, 0.35 g of surfactant A, 0.04 g of Antifoam E, 5.48 g of water were weighted into a vessel. 10 ml of glass bead (06-08 mm) were added and an aqueous isothiazoline-charcoal suspension was prepared by using a laboratory disperser (IKA® Ultra Turrax Tube disperser at 3000 rpm, 60 minutes). The suspension was stabilized by addition of 1.33 g thickener F. Moreover, 0.04 g of bactericide was added to the mixture. The mixture was further shacked for 5 minutes at 3000 rpm. Thereafter the glass beads were filtered off. The particle size was measured via using a particle size analyzer (Malvern) and was found to be: 1.6 μm (d50).

Example 2: Stability of Isothiazoline Insecticide (Photolysis on Glass Plate)

Sample was diluted to typical use rate of 75 g ai/ha, with a carrier volume of 300 L/ha—DI water was used. 10×1 μL drops of the formulation dilution deposited on glass plate. 2 glass plates per sample per time point. After application, glass plates were put in UV chamber. 1 & 24 hour(s) after application glass plates were taken out of UV chamber and washed off with 10.0 mL Water/MeOH (50/50). Wash off liquid was analyzed for active ingredient (A.I.) concentration via HPLC/MS/MS. Active Ingredient (A.I.) recovery was calculated in percentage of A.I. applied.

Results:
Compound 1

Three samples were compared: Formulation 1, Formulation 2, and compound 1 alone (dissolved in a 1:1 mixture of water/acetone). The last two were used as comparative examples.

|  | 1 hour | 24 hours |
|---|---|---|
| Formulation 1 | 57.8 | 38.6 |
| Formulation 2 | 0 | 0 |
| Compound 1 | 0 | 0 |

Compound 2

Two samples were compared: Formulation 3 and compound 2 alone (dissolved in a 1:1 mixture of water/acetone) as a comparative example.

|  | 1 hour | 24 hours |
|---|---|---|
| Formulation 3 | 50.0 | 31.0 |
| Compound 2 | 0 | 0 |

Example 3: Chromatographic Testing

LC-MS-MS method: The amount of A.I. in both wash-off and blending extracts was determined by LC-MS-MS. A calibration line was made by further diluting the spray dilution used for treating the plants.

Chromatographic Conditions:

| i. | Injection Volume: | 10 μL |
| ii. | Column: | Acquity BCH C18 |
| iii. | Temperature: | RT |
| iv. | Detector: | 4000 Q TRAP |
| v. | Auto Sampler: | CTC PAL, 100 μL Loop |
| vi. | Pump: | RHEOS 4× Ultra |
| vii. | Flow Rate: | 0.5 mL/min. |
| viii. | Retention time: | ~3.4 min |

LC Gradient:

| Time (min) | 0.1% Formic acid/Water | 0.1% Formic acid/MeOH |
|---|---|---|
| 0.1 | 80 | 20 |
| 2.0 | 50 | 50 |
| 4.0 | 1 | 99 |
| 5.9 | 1 | 99 |
| 6.0 | 80 | 20 |
| 7.0 | 80 | 20 |

Example 4: Insecticidal Activity Against Southern Armyworm (Lima Bean Leaves)

Method

Treatments were applied at 50 g ai/ha in the spray chamber at 300 L/ha. After the application, treated plants were held in both the greenhouse (which allows 50% UV penetration) and UV chamber. Plants were infested at 0, 3 and 7 Day After Treatment (DAT). The UV chamber was held at 26° C. with a 14:10 light cycle. Leaves were removed and one leaf per petri dish was infested with five $3^{rd}$ instar southern armyworm, *Spodoptera Eridania* (Stoll). Each treatment was replicated 4 times. The test was held in the holding room at 26° C. Treatments were evaluated for mortality and feeding damage at 3-7 days after infest. Results for compound 1 are reported in Table 1 and Table 2; and for compound 2 in Table 3.

TABLE 1

Residual efficacy in green house for control of Southern Armyworm using Compound 1.

| | | Mean Percent mortality Infest Date | | | | |
|---|---|---|---|---|---|---|
| Treatment | Rate gAI/HA | 0 DAT | 1 DAT | 2 DAT | 4 DAT | 7 DAT |
| Control | | 0 | 0 | 0 | 0 | 0 |
| Formulation 1 | 50 | 100 | 100 | 100 | 100 | 100 |
| Formulation 2 | 50 | 100 | 40 | 0 | 0 | 0 |

| | | Mean Percent feeding damages Infest Date | | | | |
|---|---|---|---|---|---|---|
| Treatment | Rate gAI/HA | 0 DAT | 1 DAT | 2 DAT | 4 DAT | 7 DAT |
| Control | | 100 | 100 | 100 | 100 | 98.8 |
| Formulation 1 | 50 | 3 | 4.5 | 9.3 | 12.5 | 17 |
| Formulation 2 | 50 | 1.63 | 61.3 | 98.8 | 98.3 | 98.0 |

TABLE 2

Residual efficacy under continuous UV light irradiation for control of Southern Armyworm using Compound 1.

| | | Infest Date | | | |
|---|---|---|---|---|---|
| Treatment | Rate gAI/HA | 1 DAT | 2 DAT | 4 DAT | 7 DAT |
| | | Mean Percent mortality | | | |
| Control | | 0 | 0 | 0 | 0 |
| Formulation 1 | 50 | 100 | 100 | 100 | 100 |
| Formulation 2 | 50 | 70 | 0 | 0 | 0 |
| | | Mean Percent feeding damages | | | |
| Control | | 100 | 100 | 100 | 98.8 |
| Formulation 1 | 50 | 11.0 | 16.2 | 27.5 | 48.8 |
| Formulation 2 | 50 | 67.5 | 100 | 100 | 100 |

TABLE 3

Residual efficacy in green house for control of Southern Armyworm using Compound 2.

| | | Infest Date | | | |
|---|---|---|---|---|---|
| Treatment | Rate gAI/HA | 0 DAT | 2 DAT | 5 DAT | 7 DAT |
| | | Mean Percent mortality | | | |
| Control | | 0 | 0 | 0 | 0 |
| Formulation 3 | 50 | 100 | 100 | 100 | 100 |
| | | Mean Percent feeding damages | | | |
| Control | | 100 | 100 | 100 | 98.8 |
| Formulation 3 | 50 | 4 | 21.3 | 22.5 | 27.5 |

Method:

Treatments were applied at 100 and 200 ppm in the spray chamber at 300 L/ha. Treated plants were held in the greenhouse which allows 50% UV penetration. Treatments were infested at 3, 6 and 14DAT. One leaf per petri dish was infested with five 3rd instar southern armyworm. Each treatment was replicated 4 times. After infest, the test was held in the holding room at 26° C. with no exposure to UV light. Treatments were evaluated for mortality and feeding damage at 3-4 days after infest. Results for compound 3 are reported in Table 4.

TABLE 4

Residual efficacy in green house for control of Southern Armyworm using Compound 3.

| | | Infest Date | | |
|---|---|---|---|---|
| Treatment | Rate gAI/HA | 3 DAT | 6 DAT | 14 DAT |
| | | Mean Percent mortality | | |
| Control | | 0 | 0 | 0 |
| Formulation 5 | 100 | 100 | 100 | 80 |
| Formulation 5 | 200 | 100 | 100 | 100 |
| | | Mean Percent feeding damages | | |
| Control | | 100 | 100 | 100 |
| Formulation 5 | 100 | 11.3 | 25.3 | 26.3 |
| Formulation 5 | 200 | 11 | 18.5 | 22.8 |

Example 5: Rain—Fastness

Treatments were applied at 50 g ai/ha in the spray chamber at 300 L/ha. At 1, 3, and 6 hours after application, plants were irrigated for approximately 30 min. overhead with an automated track sprayer equipped with a single 8006E nozzle with 20 mm of water. A control set of treatments was sprayed but not irrigated. After the irrigation and plants were dry, leaves were removed and one leaf per petri dish was infested with five $3^{rd}$ instar southern armyworms. Each treatment was replicated 4 times. The test was held in the holding room at 26° C. with no exposure to U.V. light. Treatments were evaluated for mortality and feeding damage at 4 days after infest (et Table 5).

TABLE 5

Rain fastness test for Compound 1:

| Treatment | Formulations | | |
|---|---|---|---|
| Irrigation timings hours | Control | Formulation 1 | Formulation 2 |
| | Mean Percent mortality | | |
| 0 | 0 | 100 | 100 |
| 1 | 0 | 100 | 100 |
| 3 | 0 | 100 | 100 |
| 6 | 0 | 100 | 100 |
| | Mean Percent feeding damages | | |
| 0 | 0 | 5.0 | 1.2 |
| 1 | 0 | 4.5 | 2.3 |
| 3 | 0 | 3.0 | 1.8 |
| 6 | 0 | 3.3 | 4.0 |

All formulations showed good rain fastness.

Example 5: Contact Trials with Southern Armyworm and Tobacco Budworm (Lima Bean Leaves)

Treatments were applied at 50 g ai/ha in the spray chamber at 300 L/ha. Southern armyworm and tobacco budworm at $3^{rd}$ instar were sprayed directly using a spray chamber application. After the application and the spray residue had dried, southern armyworm and tobacco budworm larvae were placed on untreated lima and cotton leaves respectively. Tobacco budworm larvae were placed singly on a cotton leaf in a cdi tray; 16 larvae per treatment. Southern armyworm larvae were placed on a lima bean leaf in a petri dish with five larvae per leaf and four replications. The test was held in the holding room at 26° C. with no exposure to U.V. light. Treatments were evaluated for mortality at 2 days after treatment (cf Table 6).

Dipel® DF WG formulation comprising *Bacillus thuringiensis* (54% WG) was included as a standard to confirm the methodology used in this test. Some ingestion of the compound (possibly from grooming) by TBW larvae occurred.

TABLE 6

| Efficacy of contact exposure using Compound 3. | | |
|---|---|---|
| Treatment | Rate gAI/HA | |
| | | Mean Percent mortality Southern armyworm |
| Control | | 0 |
| Formulation 3 | 50 | 100 |
| Blank of formulation 3* | 50 | 0 |
| Dipel ® DF WG | 1684 | 0 |
| | | Mean Percent mortality Tobacco Budworm |
| Control | | 0 |
| Formulation 3 | 50 | 100 |
| Blank of formulation 3 | 50 | 0 |
| Dipel ® DF WG | 1684 | 81.25 |

* Formulation 3 without active ingredient.

As Table 6 shows, Formulation 3 had excellent control for SAW and TBW as a direct contact spray application.

Example 6: Residual Efficacy for Control of *Nezara Viridula* (Tomatoes)

Treatments were applied with a spray chamber application at 300 L/ha. Treated plants were held in the greenhouse which allows 50% UV penetration and infested at 1, 4DAT and 7DAT. There were four replications per treatment. Four plants per treatment were placed inside BioQuip® cages with screened sides and infested with 20, 4th instar stink bug nymphs (*Nezara viridula*). The test was held in the holding room at 26° C. Treatments were evaluated for mortality at 4DAI (cf Table 7).

TABLE 7

| GH assay—Nezara Viridula on Tomatoes. | | | | | |
|---|---|---|---|---|---|
| | | 1DAT | | 8DAT | |
| Name | Rate gAI/HA | Live Nymphs | Percent mortality | Live Nymphs | Percent mortality |
| Formulation 3 | 200 | 2 | 89.5 | 4 | 80.0 |

Table 7 shows good residual control of *Nezara Viridula*.

We claim:
1. A composition comprising
a) a compound of the formula I.2:

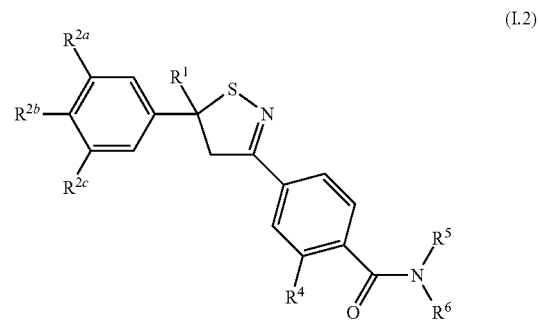

wherein
$R^1$ is $C_1$-$C_4$-haloalkyl;
$R^{2a}$, $R^{2b}$ and $R^{2c}$ are selected independently from one another from hydrogen, halogen and $C_1$-$C_2$-haloalkyl;
$R^4$ is selected from hydrogen, halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;
$R^5$ is selected from hydrogen, $C_1$-$C_6$-alkyl, $C_2$-$C_3$-alkenyl, $C_2$-$C_3$-alkynyl, —$CH_2$—CN and $C_1$-$C_6$-alkoxymethyl-; and
$R^6$ is selected from hydrogen, $C_1$-$C_6$-alkyl, $C_1$-$C_6$-haloalkyl, $C_1$-$C_4$-alkyl which carries one radical $R^8$, $C_2$-$C_6$-alkenyl, $C_2$-$C_6$-haloalkenyl, $C_2$-$C_6$-alkynyl, $C_3$-$C_6$-cycloalkyl which may be substituted by 1 to 4 substituents selected from halogen, cyano; $N(R^{10a})R^{10b}$, —CH=$NOR^9$; phenyl which may be substituted with 1, 2, 3, 4, or 5 substituents $R^{11}$, and a heteromonocyclic ring selected from rings of formulae D-1 to D-181:

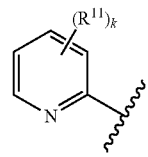

D-1

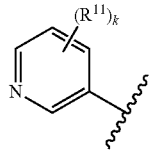

D-2

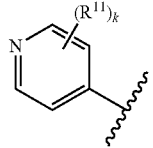

D-3

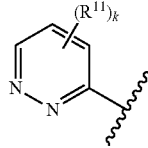

D-4

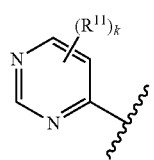 D-5
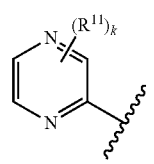 D-6
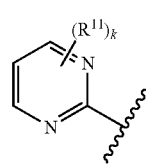 D-7
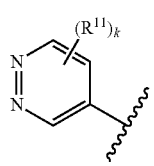 D-8
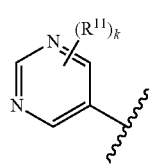 D-9
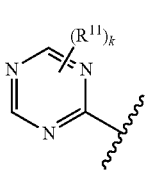 D-10
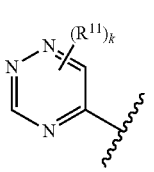 D-11
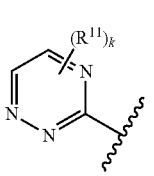 D-12
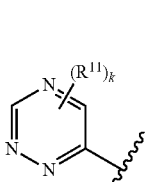 D-13
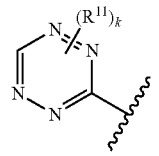 D-14
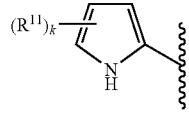 D-15
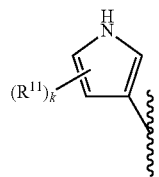 D-16
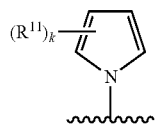 D-17
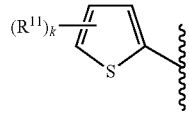 D-18
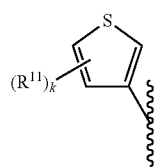 D-19
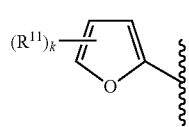 D-20
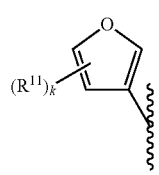 D-21
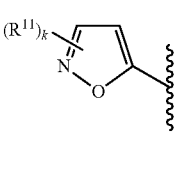 D-22
D-23

-continued
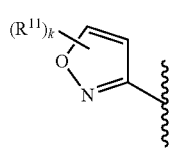 D-24
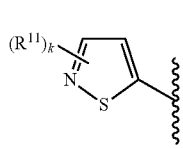 D-25
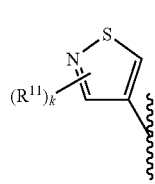 D-26
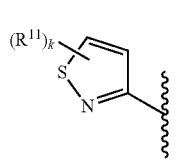 D-27
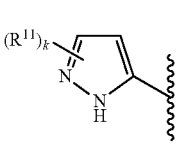 D-28
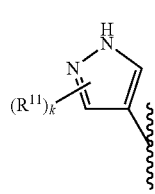 D-29
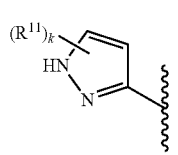 D-30
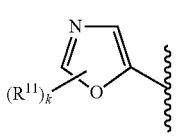 D-31
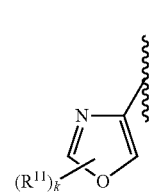 D-32
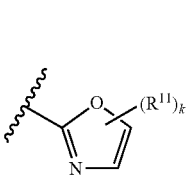 D-33
-continued
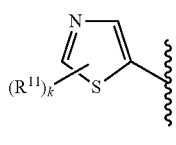 D-34
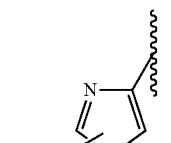 D-35
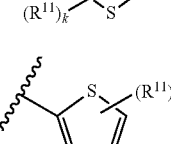 D-36
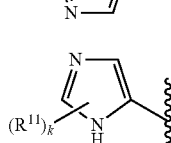 D-37
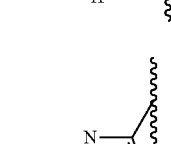 D-38
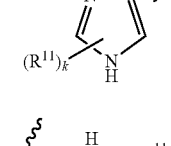 D-39
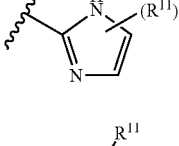 D-40
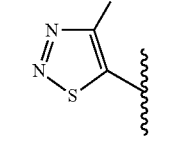 D-41
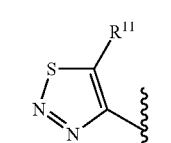 D-42
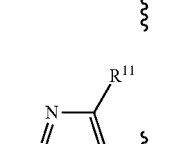 D-43

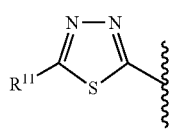 D-44
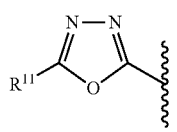 D-45
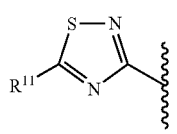 D-46
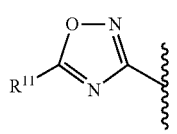 D-47
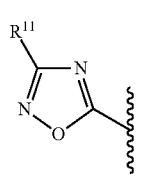 D-48
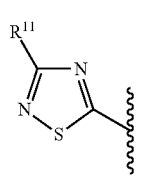 D-49
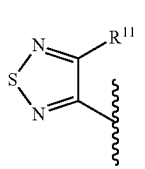 D-50
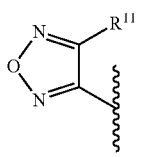 D-51
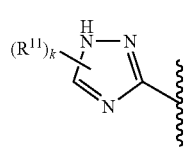 D-52
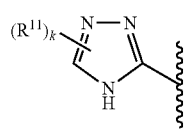 D-53
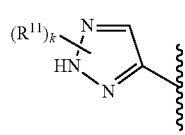 D-54
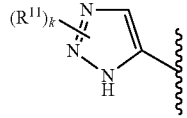 D-55
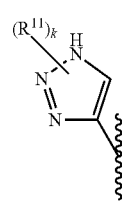 D-56
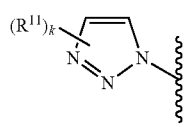 D-57
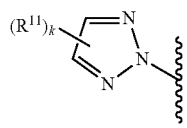 D-58
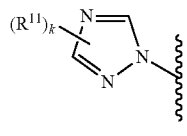 D-59
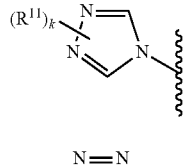 D-60
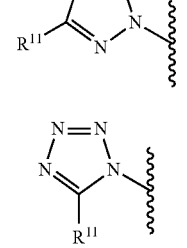 D-61
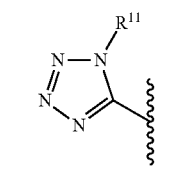 D-62
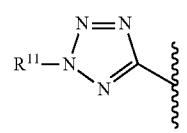 D-63
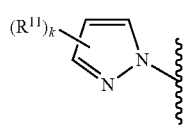 D-64
D-65

-continued
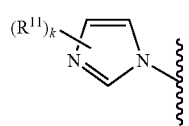 D-66
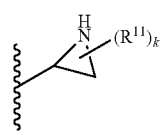 D-67
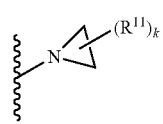 D-68
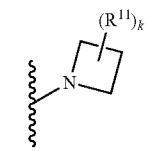 D-69
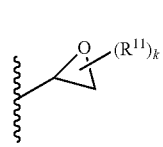 D-70
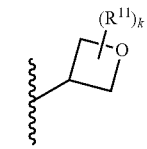 D-71
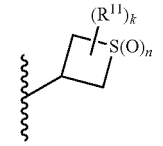 D-72
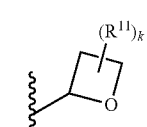 D-73
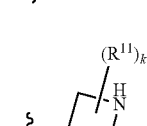 D-74
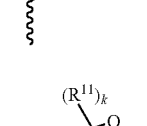 D-75
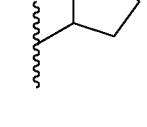
-continued
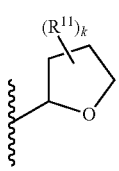 D-76
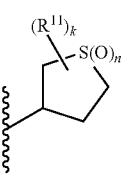 D-77
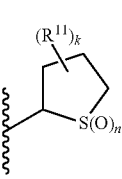 D-78
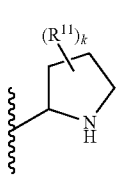 D-79
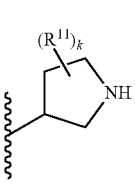 D-80
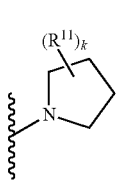 D-81
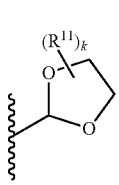 D-82
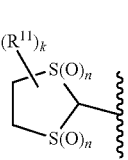 D-83
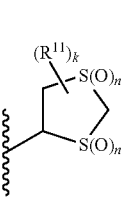 D-84

D-85 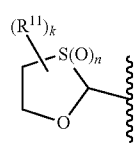
D-86 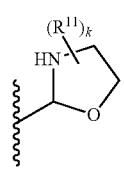
D-87 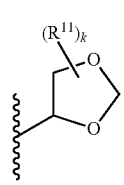
D-88 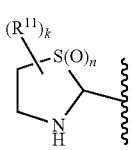
D-89 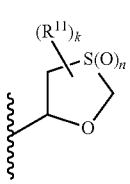
D-90 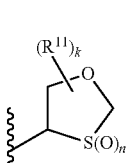
D-91 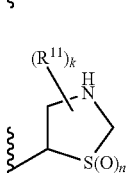
D-92 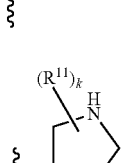
D-93 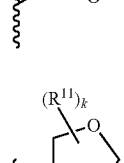
D-94 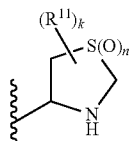
D-95 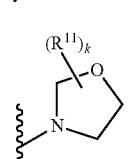
D-96 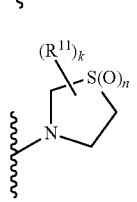
D-97 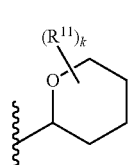
D-98 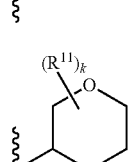
D-99 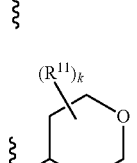
D-100 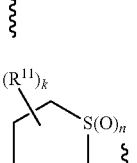
D-101 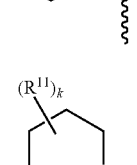
D-102 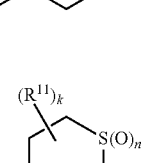

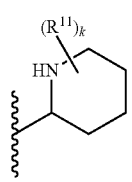 D-103
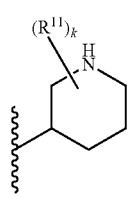 D-104
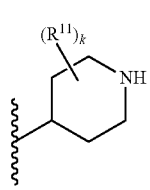 D-105
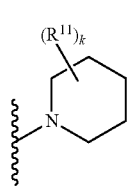 D-106
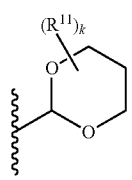 D-107
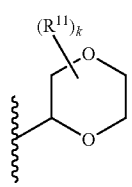 D-108
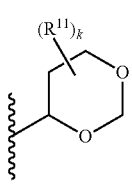 D-109
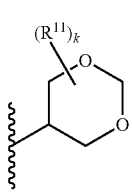 D-110
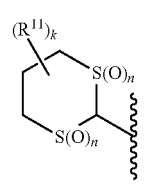 D-111
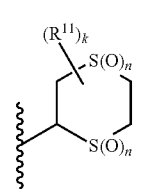 D-112
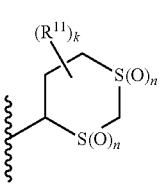 D-113
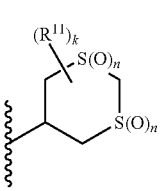 D-114
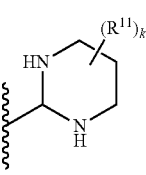 D-115
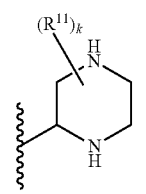 D-116
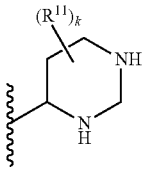 D-117
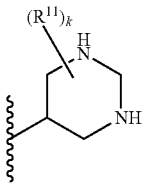 D-118

| | |
|---|---|
| D-119 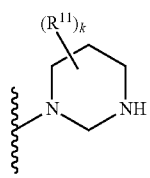 | D-128 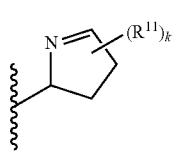 |
| D-120 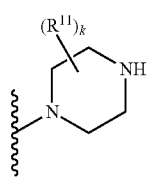 | D-129 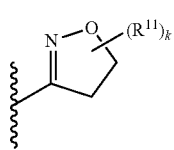 |
| D-121 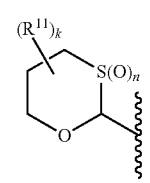 | D-130 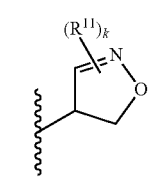 |
| D-122 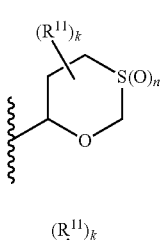 | D-131 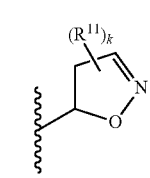 |
| D-123 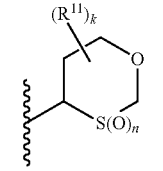 | D-132 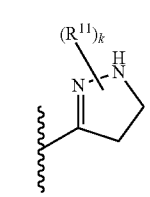 |
| D-124 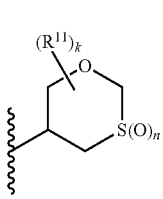 | D-133 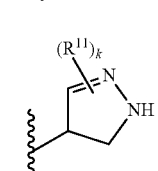 |
| D-125 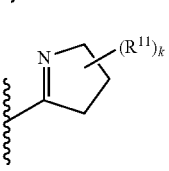 | D-134 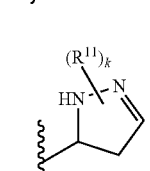 |
| D-126 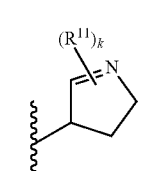 | D-135 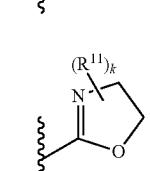 |
| D-127 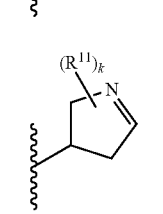 | D-136 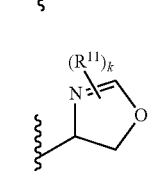 |

-continued
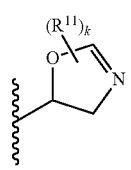 D-137
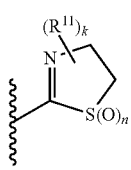 D-138
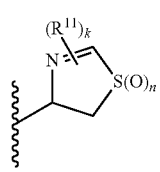 D-139
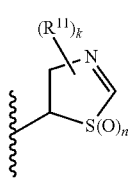 D-140
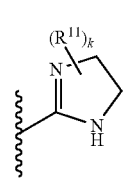 D-141
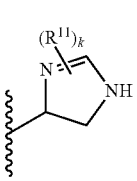 D-142
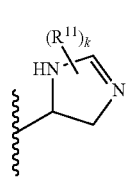 D-143
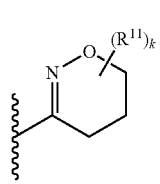 D-144
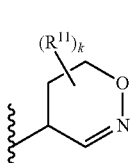 D-145
-continued
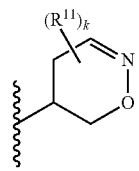 D-146
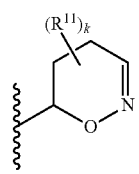 D-147
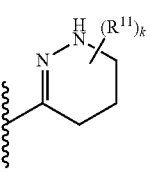 D-148
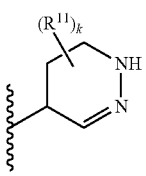 D-149
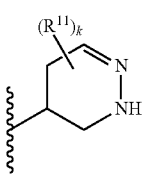 D-150
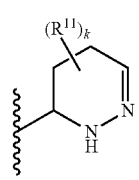 D-151
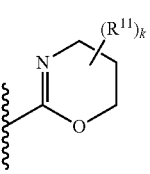 D-152
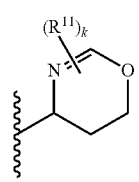 D-153
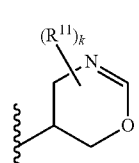 D-154

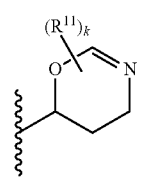 D-155
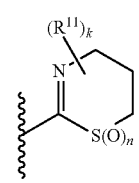 D-156
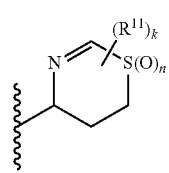 D-157
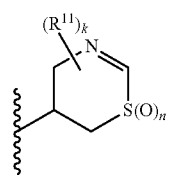 D-158
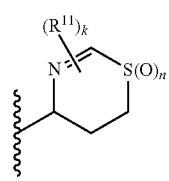 D-159
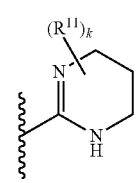 D-160
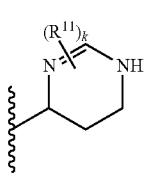 D-161
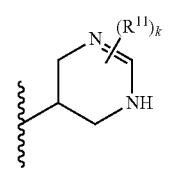 D-162
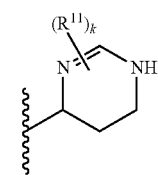 D-163
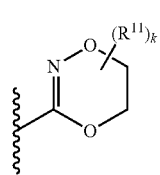 D-164
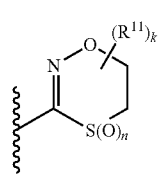 D-165
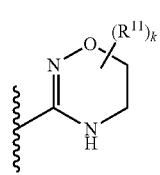 D-166
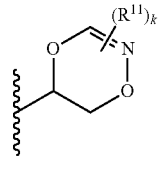 D-167
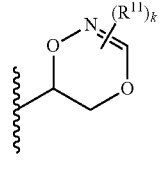 D-168
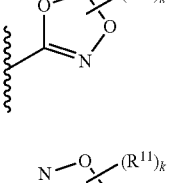 D-169
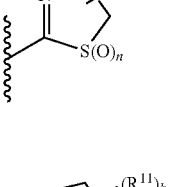 D-170
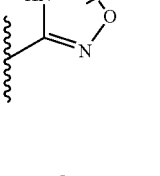 D-171
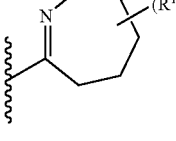 D-172

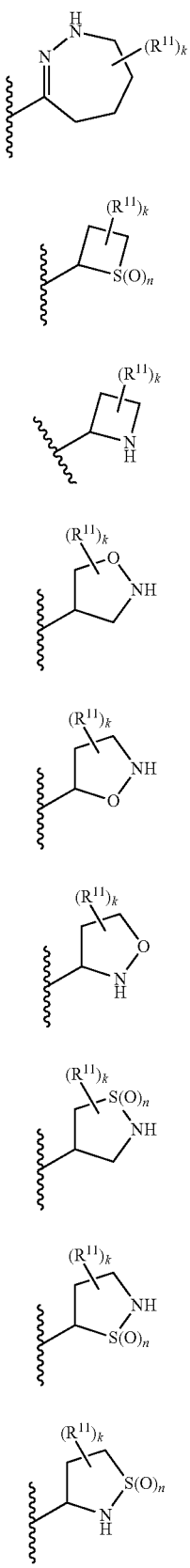

wherein
k is 0, 1, 2 or 3;
n is 0, 1 or 2; and
each $R^{11}$ is independently selected from the group consisting of halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl, $C_1$-$C_4$-alkylcarbonyl, $C_1$-$C_4$-alkylaminocarbonyl, or two $R^{11}$ present on the same carbon atom of a saturated heterocyclic ring may form together =O or =S;

$R^8$ is selected from hydrogen, OH, CN, $C_3$-$C_8$-cycloalkyl, $C_2$-$C_6$-alkenyl, $C_2$-$C_6$-alkynyl, wherein the three last-mentioned radicals may be partially or fully halogenated and/or may be substituted by one or more cyano group; $C_1$-$C_6$-alkoxy, $C_1$-$C_6$-alkylthio, $C_1$-$C_6$-alkylsulfinyl, $C_1$-$C_6$-alkylsulfonyl, wherein the four last-mentioned radicals may be partially or fully halogenated and/or may be substituted by one or more substituents selected from cyano, $C_3$-$C_6$-cycloalkyl, $C_2$-$C_6$-alkenyl, $C_2$-$C_6$-alkynyl; —C(=O)N($R^{14a}$)$R^{14b}$; phenyl, optionally substituted with 1, 2, 3, 4 or 5 substituents $R^{11}$; and a heteromonocyclic ring selected from rings of formulae D-1 to D-181;

$R^9$ is selected from hydrogen, $C_1$-$C_6$-alkyl, $C_3$-$C_6$-cycloalkyl, $C_3$-$C_6$-cycloalkylmethyl, wherein the three last-mentioned radicals may be partially or fully halogenated and/or may be substituted by one or more CN;

$R^{10a}$ is selected from the group consisting of hydrogen and $C_1$-$C_6$-alkyl;

$R^{10b}$ is selected from the group consisting of hydrogen, C(=O)N($R^{14a}$)$R^{14b}$; phenyl, optionally substituted with 1, 2, 3, 4 or 5 substituents $R^{11}$; and a heteromonocyclic ring selected from rings of formulae D-1 to D-181;

each $R^{11}$ is independently selected from the group consisting of hydrogen, halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_3$-$C_6$-cycloalkyl, $C_3$-$C_6$-halocycloalkyl, $C_2$-$C_4$-alkenyl, $C_2$-$C_4$-haloalkenyl, $C_2$-$C_4$-alkynyl and $C_2$-$C_4$-haloalkynyl, $C_1$-$C_4$-alkylcarbonyl, $C_1$-$C_4$-alkylaminocarbonyl; or two $R^{11}$ present on the same carbon atom of a saturated heterocyclic ring may form together =O or =S;

each $R^{14a}$ is selected from the group consisting of hydrogen and $C_1$-$C_6$-alkyl;

each $R^{14b}$ is selected from the group consisting of hydrogen, $C_1$-$C_6$-alkyl, $C_3$-$C_6$-cycloalkyl, $C_3$-$C_6$-cycloalkylmethyl, $C_2$-$C_4$-alkynyl, $C_2$-$C_4$-alkenyl, $C_1$-$C_4$-alkoxy, wherein the six last-mentioned radicals may be partially or fully halogenated and/or may be substituted with one cyano group;

and b) activated charcoal, wherein the composition is substantially free of a non-polar solvent; and wherein the composition is a suspension concentrate.

2. The composition according to claim 1, wherein the compound of formula 1.2 has formula I.2a:

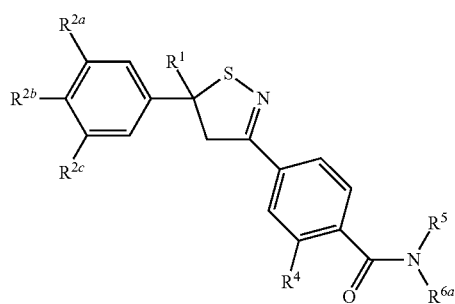

(I.2a)

wherein $R^1$ is $C_1$-$C_4$-haloalkyl and is in particular $CF_3$;

$R^{2a}$, $R^{2b}$ and $R^{2c}$ are selected independently from one another from hydrogen, halogen and $C_1$-$C_2$-haloalkyl;

$R^4$ is selected from hydrogen, halogen, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio and $C_1$-$C_4$-haloalkylthio;

$R^5$ is selected from hydrogen, $C_1$-$C_6$-alkyl, $C_2$-$C_3$-alkenyl, $C_2$-$C_3$-alkynyl, $CH_2$—CN and $C_1$-$C_6$-alkoxymethyl-; and $R^{6a}$ is selected from —X—$R^{6b}$ and —N($R^{5a}$)$R^{6c}$; wherein X is selected from —C($R^a$)$_2$—, —C($R^a$)$_2$—C($R^a$)$_2$—, —C($R^a$)$_2$—C(=O)—NR$^{10a}$—C($R^a$)$_2$—, —C($R^a$)$_2$S(O)$_n$—C($R^a$)$_2$—, —C($R^a$)$_2$—C($R^a$)$_2$—S(O)$_n$—C($R^a$)$_2$—, —C($R^a$)$_2$—O—C($R^a$)$_2$—, and —C($R^a$)$_2$—C($R^a$)$_2$—O—C($R^a$)$_2$—, wherein n is 0, 1 or 2, and each $R^a$ is independently selected from the group consisting of hydrogen, halogen, $C_1$-$C_3$-alkyl, and $C_1$-$C_3$-haloalkyl;

$R^{5a}$ is selected from hydrogen, and $C_1$-$C_6$-alkyl;

$R^{6b}$ is selected from the group consisting of $C_3$-$C_6$-cycloalkyl, $C_2$-$C_6$-alkenyl, $C_2$-$C_6$-alkynyl, wherein the three last-mentioned radicals may be partially or fully halogenated and/or may be substituted by one or more substituents $R^8$;

$R^{6c}$ is —C(=O)N($R^{14a}$)$R^{14b}$ $R^8$ is selected from, cyano, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, —C(=O)N($R^{14a}$)$R^{14b}$;

each $R^{14a}$ is selected from the group consisting of hydrogen and $C_1$-$C_6$-alkyl;

each $R^{14b}$ is selected from the group consisting of hydrogen, $C_1$-$C_6$-alkyl, $C_3$-$C_6$-cycloalkyl, $C_3$-$C_6$-cycloalkylmethyl, $C_2$-$C_4$-alkynyl, $C_2$-$C_4$-alkenyl, $C_1$-$C_4$-alkoxy, wherein the six last-mentioned radicals may be partially or fully halogenated and/or may be substituted with one cyano group;

where in case that $R^5$ is hydrogen, $R^{6a}$ is further selected from hydrogen, 1-cyanocyclopropyl, 1-cyanocyclobutyl and 1-cyanocyclopentyl;

and b) activated charcoal, wherein the composition is substantially free of a non-polar solvent; and wherein the composition is a suspension concentrate.

3. The composition of claim 1, wherein the isothiazoline insecticide is 2 to 30 wt % of the composition.

4. The composition of claim 3, wherein the solubility of the isothiazoline insecticide in water is up to 20 ppm at 20° C.

5. The composition of claim 1, wherein the isothiazoline insecticide and the activated charcoal form a complex.

6. The composition of claim 1, wherein the isothiazoline insecticide and activated charcoal are present in a ratio ranging from 1-10 wt %: 10-1 wt %.

7. A process for the preparation of the composition according to claim 1 comprising mixing of a) an isothiazoline insecticide and b) activated charcoal by wet-milling.

8. A non-therapeutic method for controlling undesired attack by insects or mites, where the composition according to claim 1 is allowed to act on the respective pests, their environment or on the crop plants to be protected from the respective pests.

9. A non-therapeutic method for controlling undesired attack by insects or mites, where the composition according to claim 2 is allowed to act on the respective pests, their environment or on the crop plants to be protected from the respective pests.

10. A non-therapeutic method for controlling undesired attack by insects or mites, where the composition according to claim 3 is allowed to act on the respective pests, their environment or on the crop plants to be protected from the respective pests.

* * * * *